(12) United States Patent
Kinney et al.

(10) Patent No.: US 7,456,014 B2
(45) Date of Patent: Nov. 25, 2008

(54) RECOMBINANT CONSTRUCTS AND THEIR USE IN REDUCING GENE EXPRESSION

(75) Inventors: Anthony J. Kinney, Wilmington, DE (US); Kevin L. Stecca, Bear, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 238 days.

(21) Appl. No.: 11/476,510

(22) Filed: Jun. 28, 2006

(65) Prior Publication Data

US 2006/0247202 A1 Nov. 2, 2006

Related U.S. Application Data

(63) Continuation of application No. 09/887,194, filed on Jun. 22, 2001, now abandoned.

(60) Provisional application No. 60/213,961, filed on Jun. 23, 2000.

(51) Int. Cl.
*C07H 21/02* (2006.01)
*C07H 21/04* (2006.01)
*C12Q 1/68* (2006.01)

(52) U.S. Cl. ................ 435/320.1; 536/23.1; 536/24.1; 536/24.5; 435/6

(58) Field of Classification Search ........................ None
See application file for complete search history.

(56) References Cited

U.S. PATENT DOCUMENTS

| | | | |
|---|---|---|---|
| 4,945,050 A | 7/1990 | Sanford et al. | |
| 5,107,065 A | 4/1992 | Shewmaker et al. | |
| 5,231,020 A | 7/1993 | Jorgensen et al. | |
| 5,510,474 A | 4/1996 | Quail et al. | |
| 5,591,616 A | 1/1997 | Hiei et al. | |
| 5,614,399 A | 3/1997 | Quail et al. | |
| 5,648,210 A | 7/1997 | Kerr et al. | |
| 5,683,439 A | 11/1997 | Jensen | |
| 5,689,049 A | 11/1997 | Cigan et al. | |
| 5,689,051 A | 11/1997 | Cigan et al. | |
| 5,773,699 A | 6/1998 | Kerr et al. | |
| 5,942,657 A | 8/1999 | Bird et al. | |

FOREIGN PATENT DOCUMENTS

| WO | WO 93/11245 A1 | 6/1993 |
|---|---|---|
| WO | WO 93/23551 A1 | 11/1993 |
| WO | WO 94/11516 A1 | 5/1994 |
| WO | WO 97/47731 A2 | 12/1997 |
| WO | WO 98/30701 A1 | 7/1998 |
| WO | WO 98/36083 A1 | 8/1998 |
| WO | WO 98/50553 A1 | 11/1998 |
| WO | WO 99/15682 A2 | 4/1999 |
| WO | WO 99/32619 A1 | 7/1999 |
| WO | WO 99/53050 A1 | 10/1999 |
| WO | WO 00/09706 A2 | 2/2000 |
| WO | WO 00/11176 A2 | 3/2000 |
| WO | WO 00/11177 A1 | 3/2000 |
| WO | WO 00/12733 A1 | 3/2000 |
| WO | WO 01/77306 A2 | 10/2001 |

OTHER PUBLICATIONS

Carolyn Napoli et. al., The Plant Cell, vol. 2:279-289, 1990, Introduction of a Chimeric Chalcone Synthase Gene Into Petunia Results in Reversible Co-Suppression of Homologous Genes in Trans.
Herve Vaucheret et. al., The Plant Journal, vol. 16:651-659, 1998, Transgene-Induced Gene Silencing in Plants.
Trisha Gura,, Nature, vol. 404:804-808, 2000, A Silence That Speaks Volumes.
Mary K. Montgomery et. al., TIG, vol. 14:255-258, 1998, Double-Stranded RNA as a Mediator in Sequence-Specific Genetic Silencing and Co-Suppression.
Andrew Fire et. al., Nature, vol. 391:806-811, 1998, Potent and Specific Genetic Interference by Double-Stranded RNA in *Caenorhabditis elegans*.
Scott M. Hammond et. al., Nature, vol. 404:293-296, 2000, An RNA-Directed Nuclease Mediates Post-Transcriptional Gene Silencing in *Drosophila* Cells.
Nicoletta Romano et. al., Molecular Microbiology, vol. 6:3343-3353, 1992, Quelling: Transient Inactivation of Gene Expression in *Neurospora crassa* by Transformation With Homologous Sequences.
Sarah R. Grant, Cell, vol. 96:303-306, 1999, Dissecting the Mechanisms of Posttranscriptional Gene Silencing: Divide and Conquer.
David C. Baulcombe, The Plant Cell, vol. 8:1833-1844, 1996, Mechanisms of Pathogen-Derived Resistance to Viruses in Transgenic Plants.
Eric U. Selker, Cell, vol. 97:157-160, 1999, Gene Silencing: Repeats That Count.
Jack K. Okamuro et al., Biochemiistry of Plants, vol. 15:-182, 1989, Regulation of Plant Gene Expression: General Principles.
Roisin Turner et al., Molecular Biotechnology, vol. 3:225-236, 1995, The Potential Exploitation of Plant Viral Translational Enhancers in Biotechnology for Increased Gene Expression.
Ivan L. W. Ingelbrect et al., The Plant Cell, vol. 1:671-680, 1989, Different 3'End Regions Strongly Influence the Level of Gene Expression in Plant Cells.
T. M. Klein et al., Nature, vol. 327:70-73, 1987, High-Velocity Microprojectiles for Delivering Nucleic Acids Into Living Cells.
Yuji Ishida et al., Nature Biotech., vol. 14:745-750, 1996, High Efficiency Transformation of Maize (Zea Mays L.) Mediated by *Agrobacterium tumefaciens*.
Jonathan D. G. Jones et al., The EMBO Journal, vol. 4:2411-2418, 1985, High Level Expression of Introduced Chimeric Genes in Regenerated Transformed Plants.
Eleanor P. De Almeida et al., Mol. Gen. Genet., vol. 218:78-86, 1989, Transgenic Expression of Two Marker Genes Under the Control of an Arabidopsis RBCS Promoter.
Taline Elmayan et al., The Plant Cell, vol. 10:1747-1757, 1998, Arabidopsis Mutants Impaired in Cosuppression.

(Continued)

*Primary Examiner*—Sean R McGarry

(57) ABSTRACT

Recombinant constructs useful for reducing the expression of endogenous mRNA and any substantially similar endogenous mRNA are disclosed. In particular, a recombinant construct comprising, inter alia, a suitable nucleic acid sequence and its reverse complement can be used to alter the expression of any homologous, endogenous RNA (i.e., the target RNA) which is in proximity to this suitable nucleic acid sequence.

2 Claims, 2 Drawing Sheets

OTHER PUBLICATIONS

Figure 1:
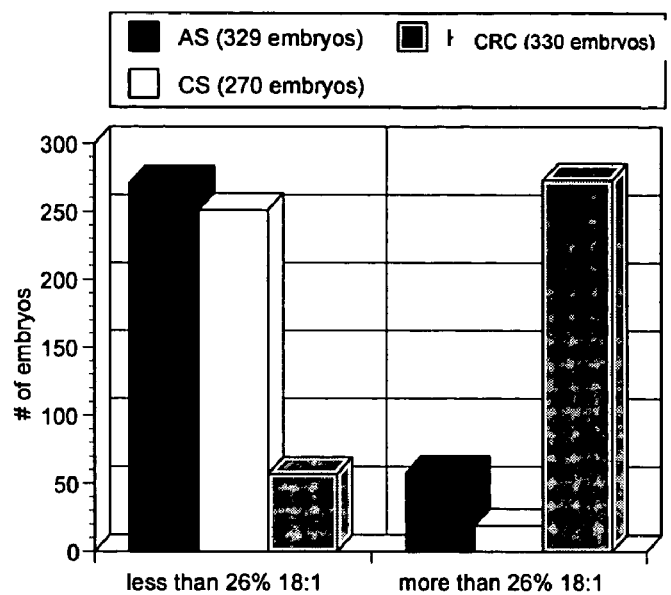

T. J. V. Higgins, Ann. Rev. Plant Phys., vol. 35:191-221, 1984, Synthesis and Regulation of Major Proteins in Seeds.

Champa Sengupta-Gopalan et al., PNAS, vol. 82:3320-3324, 1985, Developmentally Regulated Expression of the Bean-B-Phaseolin Gene in Tobacco Seed.

Leslie M. Hoffman et al., Plant Mol. Biol., vol. 11:717-729, 1988, A Modified Storage Protein is Synthesized, Processed, and Degraded in the Seeds of Transgenic Plants.

Toni Voelker et al., The EMBO Journal, vol. 6:3571-3577, 1987, Differences in Expression Between Two Seed Lectin Alleles Obtained From Normal and Lectin-Deficient Beans are Maintained in Transgenic Tobacco.

Jack K. Okamuro et. al., Proc. Natl. Acad. Sci. USA, vol. 83:8240-8244, 1986, Soybean Seed Lectin Gene and Flanking Nonseed Protein Genes are Developmentally Regulated in Transformed Tobacco Plants.

Luis Perez-Grau et. al., The Plant Cell, vol. 1:1095-1109, 1989, Soybean Seed Protein Genes are Regulated Spatially During Embryogenesis.

R. N. Beachy et. al., The EMBO Journal, vol. 4:3047-3053, 1985, Accumulation and Assembly of Soybean B-Conglycinin in Seeds of Transformed Petunia Plants.

Thomas J. V. Higgins et. al., Plant Molecular Biology, vol. 11:683-695, 1988, The Sequence of a Pea Vicilin Gene and its Expression in Transgenic Tobacco Plants.

Edward J. Newbigin et. al, Planta, vol. 180:461-470, 1990, Pea Convicilin: Structure and Primary Sequence of the Protein and Expression of a Gene in the Seeds of Transgenic Tobacco.

Anil Shirsat et. al., Mol. Gen. Genet., vol. 215:326-331, 1989, Sequences Responsible for the Tissue Specific Prometer Activity of a Pea Legumin Gene in Tobacco.

Leslie M. Hoffman et. al., The EMBO Journal, vol. 6:3213-3221, 1987, Synthesis and Protein Body Deposition of Maize 15-KD Zein in Transgenic Tobacco Seeds.

Woo S. Lee et. al., Proc. Natl. Acad. Sci. USA, vol. 88:6181-6185, 1991, Maize Oleosin is Correctly Targeted to Seed Oil Bodies in *Brassica napus* Transformed With the Maize Oleosin Gene.

Claire Marris et. al., Plant Molecular Biology, vol. 10:359-366, 1988, The 5' Flanking of a Barley B Hordein Gene Controls Tissue and Development Specific CAT Expression in Tobacco Plants.

V. Colot et. al., The EMBO Journal, vol. 6:3559-3564, 1987, Localization of Sequences in Wheat Endosperm Protein Genes Which Confer Tissue-Specifc Expression in Tobacco-.

Joel Vandekerckhove et. al., Bio/Technology, vol. 7:929-932, 1989, Enkephalins Produced in Transgenic Plants Using Modified 2S Seed Storage Proteins.

Daniel Riggs et. al., Plant Science, vol. 63:47-57, 1989, Utilization of Luciferase Fusion Genes to Monitor Differential Regulation of Phytohemagglutinin and Phaseolin Promoters in Transgenic Tobacco.

A. Boronat et. al., Plant Science, vol. 47:95-102, 1986, Isolation and Sequencing of a 28 KD Glutelin-2 From Maize. Common Elements in the 5' Flanking Regions Among Zein and Glutelin Genes.

M. Reina et. al., Nucleic Acids Research, vol. 18:6426, 1990, Sequence Analysis of a Genomic Clone Encoding a ZC2 Protein From Zea Mays W64 A.

Ralf Bernd Klosgen et. al., Mol. Gen. Genet., vol. 203:237-244, 1986, Molecular Analysis of the Waxy Locus of Zea Mays.

Alan H. Christensen et. al., Plant Molecular Biology, vol. 12:619-632, 1989, Sequence Analysis and Transcriptional Regulation by Heat Shock of Polyubiquitin Transcripts From Maize.

Gynheung An et. al., The Plant Cell, vol. 1:115-122, 1989, Functional Analysis of the 3' Control Region of the Potato Wound-Inducible Proteinase Inhibitor II Gene.

Richard A. Jefferson et. al., Proc. Natl. Acad. Sci. USA, vol. 83:8447-8451, 1986, B-Glucuronidase From *Escherichia coli* as a Gene-Fusion Marker.

Stephen F. Altschul et. al., J. Mol. Biol., vol. 215:403-410, 1990, Basic Local Alignment Search Tool.

Warren Gish et. al., Nature Genet., vol. 3:266-272, 1993, Identification of Protein Coding Regions by Database Similarity Search.

E. Cristofaro et. al., In Sugars in Nutrition, Chapter 20:313-335, 1974, Involvement of the Raffinose Family of Oligosaccharides in Flatulence.

P. M. Dey, In Biochemistry of Storage Carbohydrates in Green Plants, Chapter 2:53-129, 1985, D-Galactose-Containing Oligosaccharides.

David M. Saravitz et. al., Plant Physiol, vol. 83:185-189, 1987, Galactinol Synthase Activity and Soluble Sugars in Developing Seeds of Four Soybean Genotypes.

Norbert Sprenger et. al., The Plant Journal, vol. 21:249-258, 2000, Allocation of Raffinose Family Oligosaccharides to Transport and Storage Pools in Ajuga Reptans: The Roles of Two Distinct Galactinol Synthases.

Pei-Fang Lee et. al., Plant Physiol, vol. 100:2121-2122, 1992, Genomic Nucleotide Sequence of a Soybean Seed Maturation Protein GMPM9 Gene.

National Center for Biotechnology Information General Identifier No. M97285, Apr. 27, 1993, Hsing, Y. et. al., Genomic Nucletide Sequence of a Soybean Seed Maturation Protein GMPM9 Gene.

Sharon J. Keeler et. al., Plant Physiol, vol. 102:1009-1018, 1993, Regulation of Tobacco Acetolactate Synthase Gene Expression.

Julie R. Pear et. al., Proc. Natl. Acad. Sci. USA, vol. 93:12637-12642, 1996, Higher Plants Contain Homologs of the Bacterial Cela Genes Encoding the Catalytic Subunit of Cellulose Synthase.

Inder M. Saxena et. al., Plant Molecular Biology, vol. 15:673-683, 1990, Cloning and Sequencing of the Cellulose Synthase Catalytic Subunit Gene of Acetobacter Xylinum.

D. D. Songstad et. al., In Vitro Cell Dev. Biol. Plant, vol. 32:179-183, 1996, Production of Transgenic Maize Plants and Progeny by Bombardment of HI-II Immature Embryos.

C. L. Armstrong et. al., Maize Gen Coop Newsletter, vol. 65:92-93, 1991, Development and Availability of Germplasm With High Type II Culture Formation Response.

Kathleen D'Halluin et. al., Methods in Enzymol, vol. 216:415-426, 1992, The Bar Gene as Selectable and Screenable Marker in Plant Engineering.

Carole L. Thomas et. al., The Plant Journal, vol. 25:417-425, 2001, Size Constraints for Targeting Post-Transcriptional Gene Silencing and for RNA-Directed Methylation in Nicotiana Benthamiana Using a Potato Virus X Vector.

M. H. Kumagai et. al., Proc. Natl. Acad. Sci. USA, vol. 92:1679-1683, 1995, Cytoplasmic Inhibition of Carotenoid Biosynthesis With Virus-Derived RNA.

M. Teresa Ruiz et. al., The Plant Cell, vol. 10:937-946, 1998, Initiation and Maintenance of Virus-Induced Gene Silencing.

A. Gururaj Rao et. al., Biotechniques, vol. 8:38-40, 1990, A Quantitative Assay for B-D-Glucuronidase (GUS) Using Microtiter Plates.

W. Wohlleben et. al., Gene, vol. 70:25-37, 1988, Nucleotide Sequence of the Phosphinothricin N-Acetyltransferase Gene From Streptomyces Virido-Chromogenes TU494 and its Expression in Nicotiana Tabacum.

Levis W. Handley et. al., J. Amer. Soc. Hort. Sci., vol. 108:600-605, 1983, Relationship Between Galactinol Synthase Activity and Sugar Composition of Leaves and Seeds of Several Crop Species.

N. R. Reddy et. al., Journal of Food Science, vol. 45:1161-1164, 1980, Flatulence in Rats Following Ingestion of Cooked and Germinated Black Gram and a Fermented Product of Black Gram and Rice Blend.

Richard Gitzelmann, M.D. et. al., Pediatrics, vol. 36:231-235, 1965, The Handling of Soya Alpha-Galactosided by a Normal and a Galactosemic Child.

Abdelali Hannoufa et. al., The Plant Journal, vol. 10:459-467, 1996, The CER3 Gene of *Arabidopsis thaliana* is Expressed in Leaves, Stems, Roots, Flowers and Apical Meristems.

S. E. Radke et. al., Theor Appl Genet, vol. 75:685-694, 1988, Transformation of *Brassica napus* L. Using *Agrobacterium tumefaciens*: Developmentally Regulated Expression of a Reintroduced Napin Gene.

Edwin L. Murphy et al., J. Agr. Food Chem., vol. 20(4):813-817, 1972, Carbon Dioxide Egestion in Human Flatus.

H. Rutloff et al., Die Nahrung, vol. 11(1):39-46, 1967, Die Intestinal-Enzymatische Spaltung Von Galakto-Oligosacchariden Im Darm Von Tier Und Mensch Mit Besonderer Berucksichtigung Von *Lactobacillus bifidus*.

Chom-Kyu Chong et al., Biochem. & Biophys. Res. Comm., vol. 279:462-467, 2000, Amino Acid Residues Conferring Herbicide Tolerance in Tobacco Acetolactate Synthase.

Norihiko Misawa et al., Plant J., vol. 4(5):833-840, 1993, Functional Expression of the Erwina Uredovora Carotenoid Biosynthesis Gene CRTL in Transgenic Plants Showing an Increase of B-Carotene Biosynthesis Activity and Resistance to the Bleaching Herbicide Norflurazon.

Titia Sijen et al., RNA-Mediated Virus Resistance: Role of Repeated Transgenes and Delineation of Targeted Regions, The Plant Cell, vol. 8:2277-2294, 1996.

Maike Stam et al., Post-transcriptional silencing of chalcone synthase in Petunia by inverted transgene repeats, The Plant Journal, vol. 12(1):63-82, 1997.

R. Van Blokland et al., Post-transcriptional Suppression of Chalcone Synthase Genes in Petunia Hybrida and the Accumulation of Unspliced Pre-mRNAS, Mechanisms and Applications of Gene Silencing, Nottingham University Press, 1996, pp. 57-69.

CRC Lines Exhibit Less Chimerism Than Antisense or "Classical" Co-suppression

SEQUENCE LISTING

<160> NUMBER OF SEQ ID NOS: 36

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: ELVISLIVES
    PCR primer -continued

```
<400> SEQUENCE: 1
gaattcgcgg ccgcatggga ggtagaggtc                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of soybean Fad2-1

<400> SEQUENCE: 2
ggaaaaccat gcaacccatt ggtacttgct                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of soybean Fad2-1

<400> SEQUENCE: 3
agcaagtacc aatgggttgc atggttttcc                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of soybean Fad2-1

<400> SEQUENCE: 4
agcaagtacc aatggatact tgttcctgta                                    30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of soybean Fad2-1

<400> SEQUENCE: 5
tacaggaaca agtatccatt ggtacttgct                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:  pKS102
      linker

<400> SEQUENCE: 6
gaattcgcgg ccgcatggga ggtagaggtc                                    30

<210> SEQ ID NO 7
<211> LENGTH: 34
<212> TYPE: DNA
<213> ORGANISM: Artificial Sequence
```

```
<220> FEATURE:
<223> OTHER INFORMATION: Description of Artificial Sequence:  PCR primer
      for amplification
      of Cer3

<400> SEQUENCE: 7
ggcgcgccaa gcttggatcc gtcgacggcg cgcc                              34

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of Cer3

<400> SEQUENCE: 8
gaattcgcgg ccgcggcacg agatttgagg                                   30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of Cer3

<400> SEQUENCE: 9
ttgcccaatg tttatgcata tgtagaactg                                   30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:  PCR primer
      for amplification
      of Cer3

<400> SEQUENCE: 10
cagttctaca tatgcataaa cattgggcaa                                   30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:  ELVISLIVES
      complementary
      region of pKS106 and pKS124

<400> SEQUENCE: 11
gaattcgcgg ccgcggcacg agatttgagg                                   30

<210> SEQ ID NO 12
<211> LENGTH: 80
<212> TYPE: DNA
<213> ORGANISM: Artificial Sequence
<220> FEATURE:
<223> OTHER INFORMATION: Description of Artificial Sequence:  ELVISLIVES
      complementary
      region of pKS106 and pKS124
```

-continued

```
<400> SEQUENCE: 12
cggccggagc tggtcatctc gctcatcgtc gagtcggcgg ccgccgactc gacgatgagc      60
gagatgacca gctccggccg                                                  80

<210> SEQ ID NO 13
<211> LENGTH: 154
<212> TYPE: DNA
<213> ORGANISM: Artificial Sequence
<220> FEATURE:
<223> OTHER INFORMATION: Description of Artificial Sequence:  ELVISLIVES
      complementary
      region of pKS133

<400> SEQUENCE: 13
cggccggagc tggtcatctc gctcatcgtc gagtcggcgg ccggagctgg tcatctcgct      60
catcgtcgag tcggcggccg ccgactcgac gatgagcgag atgaccagct ccggccgccg     120
actcgacgat gagcgagatg accagctccg gccg                                 154

<210> SEQ ID NO 14
<211> LENGTH: 92
<212> TYPE: DNA
<213> ORGANISM: Artificial Sequence
<220> FEATURE:
<223> OTHER INFORMATION: Description of Artificial Sequence:  ELVISLIVES
      PCR primer

<400> SEQUENCE: 14
gaattccggc cggagctggt catctcgctc atcgtcgagt cggcggccgc cgactcgacg      60
atgagcgaga tgaccagctc cggccggaat tc                                    92

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:  ELVISLIVES
      PCR primer

<400> SEQUENCE: 15
gaattccggc cggag                                                       15

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:  PCR primer
      for amplification
      of soybean Fad2-1

<400> SEQUENCE: 16
gaattcgcgg ccgctgagtg attgctcacg agt                                   33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:  PCR primer
      for amplification
      of soybean Fad2-1

<400> SEQUENCE: 17
gaattcgcgg ccgcttaatc tctgtccata gtt                                   33
```

```
<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 5'-end

<400> SEQUENCE: 18
gaattcgcgg ccgcccaatc tattgggttc tc                               32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 3'-end of 25 nucleotide fragment

<400> SEQUENCE: 19
gaattcgcgg ccgcaacctt ggagaaccca at                               32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 3'-end 75 nucleotide fragment

<400> SEQUENCE: 20
gaattcgcgg ccgcggcatg gtgaccacac tc                               32

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 3'-end of 150 nucleotide fragment

<400> SEQUENCE: 21
gaattcgcgg ccgctgagaa ataagggact aa                               32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 3'-end 300 nucleotide fragment

<400> SEQUENCE: 22
gaattcgcgg ccgcgagtgt gacgagaaga ga                               32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 3'-end 600 nucleotide fragment
```

-continued

```
<400> SEQUENCE: 23
gaattcgcgg ccgcttctga tgaatcgtaa tg                                    32

<210> SEQ ID NO 24
<211> LENGTH: 1717
<212> TYPE: DNA
<213> ORGANISM: Artificial Sequence
<220> FEATURE:
<223> OTHER INFORMATION: Description of Artificial Sequence:  ELVISLIVES
      complementary
      region of pBS68

<400> SEQUENCE: 24
cggccggagc tggtcatctc gctcatcgtc gagtcggcgg ccgctgagtg attgctcacg        60
agtgtggtca ccatgccttc agcaagtacc aatgggttga tgatgttgtg ggtttgaccc       120
ttcactcaac actttagtc ccttatttct catggaaaat aagccatcgc cgccatcact        180
ccaacacagg ttcccttgac cgtgatgaag tgtttgtccc aaaaccaaaa tccaaagttg       240
catggttttc caagtactta aacaaccctc taggaagggc tgtttctctt ctcgtcacac       300
tcacaatagg gtggcctatg tatttagcct tcaatgtctc tggtagaccc tatgatagtt       360
ttgcaagcca ctaccaccct tatgctccca tatattctaa ccgtgagagg cttctgatct       420
atgtctctga tgttgctttg ttttctgtga cttactctct ctaccgtgtt gcaaccctga       480
aagggttggt ttggctgcta tgtgtttatg gggtgccttt gctcattgtg aacggttttc       540
ttgtgactat cacatatttg cagcacacac actttgcctt gcctcattac gattcatcag       600
aatgggactg gctgaaggga gctttggcaa ctatggacag agattaagcg gccgcatgcc       660
tccagaaaag aaagaaattt tcaagtcctt ggagggatgg gcctcggagt gggtcctacc       720
gctgctgaag cccgtggagc aatgctggca gccacaaaac ttcctccctg acccctccct       780
tccgcatgaa gagttcagcc atcaggtgaa ggagcttcgc gaacgcacta aagagttacc       840
tgatgagtac tttgtggtgc tggtgggtga tatggtcacc gaggacgcgc ttcccactta       900
ccagaccatg atcaacaacc ttgatggagt gaaagatgac agcggcacga gcccgagccc       960
gtgggccgtg tggacccggg cctggaccgc cgaggaaaac agacacgggg atctgctcag      1020
aacttatttg tatctctctg ggagggttga catggctaag gtcgaaaaga ccgtacatta      1080
cctcatttca gctggcatgg accctgggac agacaacaac ccatatttgg ggtttgtgta      1140
cacgtcattc caagagcgag caacatttgt ggcgcacggg aacacggctc ggctcgcgaa      1200
ggagggcggg gatccagtgc tggcgcgcgc gcctatgcgg gaccatcgca gcggacgaga      1260
agcggcacga gaacgcgtac tcaagaatcg tggagaagct tctggaagtg gaccccaccg      1320
gggcaatggt ggccataggg aacatgatgg agaagaagat cacgatgccg gcgcacctta      1380
tgtacgatgg ggatgacccc aggctattcg agcactactc cgctgtggcg cagcgcatag      1440
gcgtgtacac cgccaacgac tacgcagaca tcttggattt ctcgttgacg gtgaagattg      1500
gagaagcttg aaggattgat gcctgagggg aagcgggccc caggatttcc gtgtgtgggt      1560
tgcccccgag gattaggagg ttccaagaac gcgctgatga gcgagcgcgt aagatgaaga      1620
agcatcatgc cgttaagttc agttggattt tcaataaaga attgcttttg tgagcggccg      1680
ccgactcgac gatgagcgag atgaccagct ccggccg                               1717

<210> SEQ ID NO 25
<211> LENGTH: 21
<212> TYPE: DNA
<213> ORGANISM: Artificial Sequence
```

```
<220> FEATURE:
<223> OTHER INFORMATION: Description of Artificial Sequence:   PCR primer
      for amplification
      of soybean Lea promoter 5'-end

<400> SEQUENCE: 25
attaacctca attcttctaa g                                              21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:   PCR primer
      for amplification
      of soybean Lea promoter 3'end

<400> SEQUENCE: 26
ttcaaagatc aattatttcc                                                20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:   PCR primer
      for amplification
      of phaseolin terminator 5'-end

<400> SEQUENCE: 27
catggccacg tgcatgaagt at                                             22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:   PCR primer
      for amplification
      of phaseolin terminator 3'-end

<400> SEQUENCE: 28
atccctgaag tgtctcattt ta                                             22

<210> SEQ ID NO 29
<211> LENGTH: 963
<212> TYPE: DNA
<213> ORGANISM: Artificial Sequence
<220> FEATURE:
<223> OTHER INFORMATION: Description of Artificial Sequence:   ELVISLIVES
      complementary
      region of pKS149

<400> SEQUENCE: 29
cggccggagc tggtcatctc gctcatcgtc gagtcggcgg ccgctgagct gatttaaatc     60
accactgtca aaaccaccat caccgacgct caagccaagg tcgccaccga tcatggtcgt    120
gcctacgtca ccttcctcgc cggaaacggt gactatgtga aggtgtcgt tggcttggca     180 aaaggtctga gaaaagtgaa gagcatgtac cctctggtgg ttgcagtgct acccgatgtt    240
ccccaagatc accgcaacat tctcacctcc caaggttgca ttgttagaga gattgagccc    300 gtgtacccc cagagaatca aacccagttt gccatggcat attacgtcat caactattcc    360
aagctacgta tttgggagtt tgtggagtac agcaagatga tatacctaga cggtgatatc    420 caagttttg acaacattga ccacttggga tcgatcctga gctgatttaa accaccgttg    480
```

```
ttgccaatgt caccaccgag caattaccca aggctcgtgg aggaagtggg cgtgccttcg      540
tgacctttct tgctgggaac ggtgattacg taaagggtgt cgtgggtttg gccaaaggac      600
tgagaaaggc caaaagcatg tacccttttgg tggttgctgt gttaccagat gttcctgaag     660
aacatcgtga gattctcaaa tcccaaggtt gcattgtcag ggagattgaa cctgtgtacc      720
ctcctgagaa ccagacccag ttcgtcatgg cctattatgt catcaattac tccaagctac      780
gtatttggga gttcgtggag tacaagaaga cgatatacct agacggtgac atccaagtat      840
ttggaaacat agaccacttg tttgatctgt gagctgattt aagcggccgc cgactcgacg      900
atgagcgaga tgaccagctc cggccgccga ctcgacgatg agcgagatga ccagctccgg      960
ccg                                                                    963
```

<210> SEQ ID NO 30
<211> LENGTH: 987
<212> TYPE: DNA
<213> ORGANISM: Glycine max

<400> SEQUENCE: 30

```
atggctccta atatcaccac tgtcaaaacc accatcaccg acgctcaagc caaggtcgcc       60
accgatcatg gtcgtgccta cgtcaccttc ctcgccggaa acggtgacta tgtgaaaggt      120
gtcgttggct tggcaaaagg tctgagaaaa gtgaagagca tgtaccctct ggtggttgca      180
gtgctacccg atgttcccca agatcaccgc aacattctca cctcccaagg ttgcattgtt      240
agagagattg agcccgtgta cccccccagag aatcaaaccc agtttgccat ggcatattac     300
gtcatcaact attccaagct acgtatttgg gagtttgtgg agtacagcaa gatgatatac      360
ctagacggtg atatccaagt ttttgacaac attgaccact tgtttgactt gcctgataac      420
tacttctatg cggtgatgga ctgtttctgt gagccaactt ggggccacac taaacaatat      480
cagatcggtt actgccagca gtgccccccat aaggttcagt ggcccactca ctttgggccc     540
aaacctcctc tctatttcaa tgctggcatg tttgtgtatg agcccaattt ggctacttac      600
cgtgacctcc ttcaaacagt ccaagtcacc cagcccactt cctttgctga acaggatttt      660
ttgaacatgt acttcaagga caaatatagg ccaattccta atgtctacaa tcttgtgctg      720
gccatgctgt ggcgtcaccc tgagaacgtt gagcttgaca agttaaaagt ggttcactac      780
tgtgctgctg gtctaagcc ttggaggtac actgggaagg aggagaatat ggagagagaa       840
gatatcaaga tgttagtgaa aaagtggtgg gatatatatg aggatgagac tttggactac      900
aacaatccac tcaatgtgga taagttcact gcggcactta tggaggttgg tgaagtcaag      960
ttcgtccgtg ccccatctgc tgcttaa                                          987
```

<210> SEQ ID NO 31
<211> LENGTH: 328
<212> TYPE: PRT
<213> ORGANISM: Glycine max

<400> SEQUENCE: 31

```
Met Ala Pro Asn Ile Thr Thr Val Lys Thr Thr Ile Thr Asp Ala Gln
                 5                  10                  15

Ala Lys Val Ala Thr Asp His Gly Arg Ala Tyr Val Thr Phe Leu Ala
            20                  25                  30

Gly Asn Gly Asp Tyr Val Lys Gly Val Val Gly Leu Ala Lys Gly Leu
        35                  40                  45

Arg Lys Val Lys Ser Met Tyr Pro Leu Val Val Ala Val Leu Pro Asp
    50                  55                  60
```

```
Val Pro Gln Asp His Arg Asn Ile Leu Thr Ser Gln Gly Cys Ile Val
 65                  70                  75                  80

Arg Glu Ile Glu Pro Val Tyr Pro Pro Glu Asn Gln Thr Gln Phe Ala
                 85                  90                  95

Met Ala Tyr Tyr Val Ile Asn Tyr Ser Lys Leu Arg Ile Trp Glu Phe
            100                 105                 110

Val Glu Tyr Ser Lys Met Ile Tyr Leu Asp Gly Asp Ile Gln Val Phe
        115                 120                 125

Asp Asn Ile Asp His Leu Phe Asp Leu Pro Asp Asn Tyr Phe Tyr Ala
130                 135                 140

Val Met Asp Cys Phe Cys Glu Pro Thr Trp Gly His Thr Lys Gln Tyr
145                 150                 155                 160

Gln Ile Gly Tyr Cys Gln Gln Cys Pro His Lys Val Gln Trp Pro Thr
                165                 170                 175

His Phe Gly Pro Lys Pro Pro Leu Tyr Phe Asn Ala Gly Met Phe Val
            180                 185                 190

Tyr Glu Pro Asn Leu Ala Thr Tyr Arg Asp Leu Leu Gln Thr Val Gln
        195                 200                 205

Val Thr Gln Pro Thr Ser Phe Ala Glu Gln Asp Phe Leu Asn Met Tyr
210                 215                 220

Phe Lys Asp Lys Tyr Arg Pro Ile Pro Asn Val Tyr Asn Leu Val Leu
225                 230                 235                 240

Ala Met Leu Trp Arg His Pro Glu Asn Val Glu Leu Asp Lys Val Lys
                245                 250                 255

Val Val His Tyr Cys Ala Ala Gly Ser Lys Pro Trp Arg Tyr Thr Gly
            260                 265                 270

Lys Glu Glu Asn Met Glu Arg Glu Asp Ile Lys Met Leu Val Lys Lys
        275                 280                 285

Trp Trp Asp Ile Tyr Glu Asp Glu Thr Leu Asp Tyr Asn Asn Pro Leu
290                 295                 300

Asn Val Asp Lys Phe Thr Ala Ala Leu Met Glu Val Gly Glu Val Lys
305                 310                 315                 320

Phe Val Arg Ala Pro Ser Ala Ala
                325

<210> SEQ ID NO 32
<211> LENGTH: 1350
<212> TYPE: DNA
<213> ORGANISM: Glycine max

<400> SEQUENCE: 32
gcacgagaaa caaccaacct cttcagtgat ctttgattag tactaagcta aaccatttct      60
tattccctca aaatcaaaac cttttctctt ctagctattt ccctttcaa atcatgccac     120 ctaacatcac caccgttgtt gccaatgtca ccaccgagca attacccaag gctcgtggag     180
gaagtgggcg tgccttcgtg acctttcttg ctgggaacgg tgattacgta aagggtgtcg     240
tgggtttggc caaaggactg agaaaggcca aaagcatgta cccctttggtg gttgctgtgt     300 taccagatgt tcctgaagaa catcgtgaga ttctcaaatc ccaaggttgc attgtcaggg     360
agattgaacc tgtgtaccct cctgagaacc agacccagtt cgccatggcc tattatgtca     420
tcaattactc caagctacgt atttgggagt tcgtggagta caagaagacg atatacctag     480
acggtgacat ccaagtattt ggaaacatag accacttgtt tgatctgcct gataattatt     540
tctatgcggt gatggattgt ttctgcgaga agacttggag ccacacccct cagttccaga     600
```

```
ttgggtactg ccaacagtgc cctgataagg ttcaatggcc ctctcacttt ggttccaaac       660
ctcctctata tttcaatgct ggcatgtttg tttatgagcc taatctcgac acctaccgtg       720
atcttctcca aactgtccaa ctcaccaagc ccacttcttt tgctgagcag gactttctca       780
acatgtactt caaggacaag tacaagccaa taccgaacat gtacaacctt gtgctggcca       840
tgttgtggcg tcaccctgaa atgttgaac ttgataaagt tcaagtggtt cattactgtg        900
ctgctgggtc taagccttgg aggttcactg ggaaggaaga gaacatggat agggaagata       960
tcaagatgct tgtgaagaag tggtgggaca tatatgaaga tgagacactg gactacaata      1020
acaactctgt caacgtggaa cgtttcacat cggcactatt ggatgctggg ggctttcagt      1080
ttgtgccagc accttctgct gcctaatatg cttattattt acagctacaa attaatgtta      1140
attaacgaca agtatatgt attgttattt gctttttttc gttttttgggt cttatatatg      1200 aaggaacaac gtctatggtt ttaatttgga tgaccttctt gtatacaaag ccacatgtga      1260
tctcatacag cttttgatta ttattaagaa attagaggac cttttattat gagtccttta     1320
cttaaaaaaa aaaaaaaaaa aaaaaaaaa                                        1350
```

<210> SEQ ID NO 33
<211> LENGTH: 358
<212> TYPE: PRT
<213> ORGANISM: Glycine max

<400> SEQUENCE: 33

```
Ser Leu Ile Ser Thr Lys Leu Asn His Phe Leu Phe Pro Gln Asn Gln
  1               5                  10                  15

Asn Leu Phe Leu Ser Ser Tyr Phe Pro Phe Gln Ile Met Pro Pro Asn
             20                  25                  30

Ile Thr Thr Val Val Ala Asn Val Thr Thr Glu Gln Leu Pro Lys Ala
         35                  40                  45

Arg Gly Gly Ser Gly Arg Ala Phe Val Thr Phe Leu Ala Gly Asn Gly
     50                  55                  60

Asp Tyr Val Lys Gly Val Val Gly Leu Ala Lys Gly Leu Arg Lys Ala
 65                  70                  75                  80

Lys Ser Met Tyr Pro Leu Val Val Ala Val Leu Pro Asp Val Pro Glu
                 85                  90                  95

Glu His Arg Glu Ile Leu Lys Ser Gln Gly Cys Ile Val Arg Glu Ile
            100                 105                 110

Glu Pro Val Tyr Pro Pro Glu Asn Gln Thr Gln Phe Ala Met Ala Tyr
        115                 120                 125

Tyr Val Ile Asn Tyr Ser Lys Leu Arg Ile Trp Glu Phe Val Glu Tyr
    130                 135                 140

Lys Lys Thr Ile Tyr Leu Asp Gly Asp Ile Gln Val Phe Gly Asn Ile
145                 150                 155                 160

Asp His Leu Phe Asp Leu Pro Asp Asn Tyr Phe Tyr Ala Val Met Asp
                165                 170                 175

Cys Phe Cys Glu Lys Thr Trp Ser His Thr Pro Gln Phe Gln Ile Gly
            180                 185                 190

Tyr Cys Gln Gln Cys Pro Asp Lys Val Gln Trp Pro Ser His Phe Gly
        195                 200                 205

Ser Lys Pro Pro Leu Tyr Phe Asn Ala Gly Met Phe Val Tyr Glu Pro
    210                 215                 220

Asn Leu Asp Thr Tyr Arg Asp Leu Leu Gln Thr Val Gln Leu Thr Lys
225                 230                 235                 240
```

```
Pro Thr Ser Phe Ala Glu Gln Asp Phe Leu Asn Met Tyr Phe Lys Asp
                245                 250                 255

Lys Tyr Lys Pro Ile Pro Asn Met Tyr Asn Leu Val Leu Ala Met Leu
            260                 265                 270

Trp Arg His Pro Glu Asn Val Glu Leu Asp Lys Val Gln Val Val His
        275                 280                 285

Tyr Cys Ala Ala Gly Ser Lys Pro Trp Arg Phe Thr Gly Lys Glu Glu
    290                 295                 300

Asn Met Asp Arg Glu Asp Ile Lys Met Leu Val Lys Lys Trp Trp Asp
305                 310                 315                 320

Ile Tyr Glu Asp Glu Thr Leu Asp Tyr Asn Asn Ser Val Asn Val
                325                 330                 335

Glu Arg Phe Thr Ser Ala Leu Leu Asp Ala Gly Gly Phe Gln Phe Val
            340                 345                 350

Pro Ala Pro Ser Ala Ala
        355

<210> SEQ ID NO 34
<211> LENGTH: 515
<212> TYPE: DNA
<213> ORGANISM: Artificial Sequence
<220> FEATURE:
<223> OTHER INFORMATION: Description of Artificial Sequence: SHH3
      complementary
      region of PHP17939

<400> SEQUENCE: 34
gttaacagct ttatttgttc taggttgttc atgaaatatt tttttggttt tatctccgtt    60
gtaagaaaat catgtgcttt gtgtcgccac tcactattgc agcttttca tgcattggtc    120 agattgacgg ttgattgtat ttttgttttt tatggttttg tgttatgact taagtcttca    180
tctctttatc tcttcatcag gtttgacggt tacttaatat ggtgcatgca tgggtacatc    240
actagaaacc atggaaggta ccaagatatc aaccgcggaa agatcgtaca aatggcatgt    300
taaataaccg tcaaacctga tgaagagata aagagatgaa gacttaagtc ataacacaaa    360
accataaaaa acaaaaatac aatcaaccgt caatctgacc aatgcatgaa aaagctgcaa    420
tagtgagtgg cgacacaaag cacatgattt tcttacaacg gagataaaac caaaaaaata    480
tttcatgaac aacctagaac aaataaagcg ttaac                              515

<210> SEQ ID NO 35
<211> LENGTH: 1968
<212> TYPE: DNA
<213> ORGANISM: Glycine max

<400> SEQUENCE: 35
atgccacaca acacaatggc ggccaccgct tccagaacca cccgattctc ttcttcctct    60
tcacacccca ccttccccaa acgcattact agatccaccc tccctctctc tcatcaaacc    120
ctcaccaaac ccaaccacgc tctcaaaatc aaatgttcca tctccaaacc ccccacggcg    180
gcgcccttca ccaaggaagc gccgaccacg gagcccttcg tgtcacggtt cgcctccggc    240
gaacctcgca agggcgcgga catccttgtg gaggcgctgg agaggcaggg cgtgacgacg    300
gtgttcgcgt accccggcgg tgcgtcgatg gagatccacc aggcgctcac gcgctccgcc    360
gccatccgca acgtgctccc gcgccacgag cagggcggcg tcttcgccgc cgaaggctac    420
gcgcgttcct ccggcctccc cggcgtctgc attgccacct ccggcccggg cgccaccaac    480
ctcgtgagcg gcctcgccga cgctttaatg gacagcgtcc cagtcgtcgc catcaccggc    540
```

```
caggtcgccc gccggatgat cggcaccgac gccttccaag aaacccgat cgtggaggtg      600 agcagatcca tcacgaagca caactacctc atcctcgacg tcgacgacat ccccgcgtc      660 gtcgccgagg ctttcttcgt cgccacctcc ggccgcccg gtccggtcct catcgacatt      720
cccaaagacg ttcagcagca actcgccgtg cctaattggg acgagcccgt taacctcccc    780
ggttacctcg ccaggctgcc caggcccccc gccgaggccc aattggaaca cattgtcaga    840
ctcatcatgg aggcccaaaa gcccgttctc tacgtcggcg gtggcagttt gaattccagt    900
gctgaattga ggcgctttgt tgaactcact ggtattcccg ttgctagcac tttaatgggt    960
cttggaactt ttcctattgg tgatgaatat tcccttcaga tgctgggtat gcatggtact    1020
gtttatgcta actatgctgt tgacaatagt gatttgttgc ttgcctttgg ggtaaggttt    1080
gatgaccgtg ttactgggaa gcttgaggct tttgctagta gggctaagat tgttcacatt    1140
gatattgatt ctgccgagat tgggaagaac aagcaggcgc acgtgtcggt ttgcgcggat    1200
ttgaagttgg ccttgaaggg aattaatatg attttggagg agaaaggagt ggagggtaag    1260
tttgatcttg gaggttggag agaagagatt aatgtgcaga acacaagtt tccattgggt     1320 tacaagacat tccaggacgc gatttctccg cagcatgcta tcgaggttct tgatgagttg    1380
actaatggag atgctattgt tagtactggg gttgggcagc atcaaatgtg ggctgcgcag    1440
ttttacaagt acaagagacc gaggcagtgg ttgacctcag ggggtcttgg agccatgggt    1500
tttggattgc ctgcggctat tggtgctgct gttgctaacc ctggggctgt tgtggttgac    1560
attgatgggg atggtagttt catcatgaat gttcaggagt tggccactat aagagtggag    1620
aatctcccag ttaagatatt gttgttgaac aatcagcatt tgggtatggt ggttcagttg    1680
gaggataggt tctacaagtc caatagagct cacacctatc ttggagatcc gtctagcgag    1740
agcgagatat tcccaaacat gctcaagttt gctgatgctt gtgggatacc ggcagcgcga    1800
gtgacgaaga aggaagagct tagagcggca attcagagaa tgttggacac ccctggcccc    1860
taccttcttg atgtcattgt gccccatcag gagcatgtgt tgccgatgat tcccagtaat    1920
ggatccttca aggatgtgat aactgagggt gatggtagaa cgaggtac                 1968
```

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: PCR primer
      for amplification
      of soybean Fad2-1, 3'-end 50 nucleotide fragment

<400> SEQUENCE: 36

```
gaattcgcgg ccgcatcacc cacacaccag tg                                   32
```

RECOMBINANT CONSTRUCTS AND THEIR USE IN REDUCING GENE EXPRESSION

FIELD OF THE INVENTION

This invention relates to reducing gene expression and, in particular, to recombinant constructs useful for reducing the expression of endogenous mRNA and any substantially similar endogenous mRNA.

BACKGROUND OF THE INVENTION

Plant development is a complex physiological and biochemical process requiring the coordinated expression of many genes. The production of new plant varieties with improved nutritional or disease-resistant traits can be achieved by modifying this coordinated pattern of gene expression. Recombinant DNA techniques have made it possible to alter the expression patterns of individual, specific plant genes without directly affecting the expression of other plant genes. In this way, the expression pattern of an individual gene can be either enhanced or diminished in the whole plant, in specific tissues, or in developmental stages. Thus, it is now routine to construct transgenes with defined promoters and terminators and express them in a variety of organisms.

However, there are some reports in the literature that some introduced transgenes do not have the expected expression patterns. These unexpected expression patterns are seen in organisms as diverse as nematodes and plants. For example, some plants receiving transgenic copies of an endogenous gene under the control of a strong promoter, sometimes fail to accumulate mRNA for that gene. Furthermore, all mRNA from endogenous genes having sequence homology to the transgene also fail to accumulate mRNA, effectively eliminating the expression of the endogenous gene product. This was discovered originally when chalcone synthase transgenes in petunia caused suppression of the endogenous chalcone synthase genes (Napoli et al (1990) *Plant Cell* 2:279-289).

The phenomenon was referred to as "cosuppression" since expression of both the endogenous gene and the introduced transgene were suppressed (for reviews see Vaucheret et al (1998) *Plant J* 16:651-659; and Gura (2000) *Nature* 404:804-808). Cosuppression technology constitutes the subject matter of U.S. Pat. No. 5,231,020 which issued to Jorgensen et al on Jul. 27, 1999. Cosuppression is also referred to as "gene silencing" or post-transcriptional gene silencing (PTGS) by plant biologists, "RNA interference" by those studying worms and flies (Montgomery and Fire (1998) *TIG* 14:255-258; Fire et al (1998) *Nature* 391:806-811; Hammond et al (2000) *Nature* 404:293-296; and PCT Application No. WO 99/32619 published Jul. 1, 1999), and "quelling" by researchers working with fungi (Romano and Macino (1992) *Mol Microbiol* 6:3343-3353).

The mechanisms by which the expression of a specific gene is inhibited by either antisense or sense RNA genes are not clearly understood and the frequencies of obtaining the desired down regulation in a transgenic plant are generally low and vary with the gene, the strength of its promoter and specificity, the method of transformation, and the complexity of transgene insertion events. (Grant (1999) *Cell* 96:303-306; and Selker (1999) *Cell* 97:157-160.)

The speculation is that PTGS is an ancient self-defense mechanism evolved to combat infection by viruses and transposons. It appears that this pathogen-derived resistance is triggered by the presence in the host's cells of double-stranded RNA (dsRNA) or some other aberrant nucleic acid, which are indicative of a viral assault. Normally, the RNA moving freely around a cell should be single-stranded messenger RNA (mRNA) which is the intermediate between host genes and the proteins they encode. When the aberrant RNA invades then any mRNAs matching the invading nucleic acid's sequence are shut down. If the trigger is homologous to part of the host's genetic sequence, then both the host and viral genes are silenced (Baulcombe (1996) *Plant Cell* 8:1833-1844). WO 99/15682 which published on Apr. 1, 1999 and WO 98/36083 which published on Aug. 20, 1998 describe gene silencing materials and methods. These publications describe, inter alia, the silencing of plant genomic gene expression by introducing expression constructs containing plant viral nucleic acid sequences coupled to whole, or partial, gene sequences homologous to the target genes to be silenced.

WO 99/53050, which published on Oct. 21, 1999, describes chimeric constructs encoding RNA molecules directed towards a target nucleic acid which are comprised of sense and antisense sequences, such that the expressed RNA is capable of forming an intramolecular double-stranded RNA structure. The expression of these RNA in transgenic organisms results in gene silencing of the all homologous target nucleic acid sequences within the cell.

U.S. Pat. No. 5,942,657, issued to Bird et al on Aug. 25, 1999, and WO 93/23551, which published on Nov. 25, 1993, describe coordinated inhibition of plant gene expression in which two or more genes are inhibited by introducing a single control gene having distinct DNA regions homologous to each of the target genes and a promoter operable in plants adapted to transcribe from such distinct regions RNA that inhibits expression of each of the target genes.

The present invention describes the use of suitable DNA sequences or RNA sequences derived therefrom, as is discussed below, in ways which here-to-fore have not been previously described. These sequences, and their reverse complements, can be used to reduce the expression of any endogenous genomic sequence that shares substantial similarity to nucleic acid fragment which is in proximity to the DNA sequence or RNA sequence derived therefrom. The details of this phenomenon are described herein.

SUMMARY OF THE INVENTION

This invention concerns a recombinant construct comprising a promoter operably linked to a DNA sequence which, when expressed by a host produces an RNA having:

(a) homology to at least one target mRNA expressed by the host, (b) two complementary RNA regions which are unrelated to any endogenous RNA in the host, and which are in proximity to (a), wherein the expressed RNA reduces the expression of the target mRNA or any substantially similar endogenous mRNA.

In a second embodiment, this invention concerns a recombinant construct comprising a promoter operably linked to a DNA sequence which, when expressed by a host, produces an RNA having:

(a) homology to at least one target mRNA expressed by the host, (b) an RNA region unrelated to any endogenous RNA in the host and located 5' to (a), and (c) the reverse complement of the RNA in (b) located 3' to (a), wherein the expressed RNA reduces the expression of the target mRNA or any substantially similar endogenous mRNA.

In a third embodiment, this invention concerns a recombinant construct comprising a promoter operably linked to a DNA sequence which, when expressed by a host, produces an RNA having:

(a) homology to at least one target mRNA expressed by the host, and (b) two complementary RNA regions which are unrelated to any endogenous RNA in the host, and which are located 5' to (a), wherein the expressed RNA reduces the expression of the target mRNA or any substantially similar endogenous mRNA.

In a fourth embodiment, this invention concerns a recombinant construct comprising a promoter operably linked to a DNA sequence which, when expressed by a host, produces an RNA having:

(a) homology to at least one target mRNA expressed by the host, and (b) two complementary RNA regions which are unrelated to any endogenous RNA in the host, and which are located 3' to (a), wherein the expressed RNA reduces the expression of the target mRNA or any substantially similar endogenous mRNA.

In a fifth embodiment, this invention concerns a recombinant construct comprising a promoter operably linked to a DNA sequence which, when expressed by a host, produces an RNA having:

(a) homology to at least one target mRNA expressed by the host, and (b) two complementary RNA regions which are unrelated to any endogenous RNA in the host, and which are located within (a), wherein the expressed RNA reduces the expression of the target mRNA or any substantially similar endogenous mRNA.

In another aspect of any of the foregoing recombinant constructs, the RNA region or regions which are unrelated to any endogenous RNA in the host comprise a synthetic, non-naturally occurring RNA sequence.

In still another aspect of any of the foregoing recombinant constructs, the RNA region or regions which are unrelated to any endogenous RNA in the host do not comprise plant viral RNA.

In a sixth embodiment, this invention concerns a method for reducing expression of a target mRNA or any substantially similar endogenous mRNA which comprises:

(a) transforming a host with any of the above-described recombinant constructs; and (b) selecting hosts which have reduced expression of the target mRNA or any substantially similar endogenous mRNA.

In a seventh, embodiment, this invention concerns a recombinant construct comprising an RNA having:

(a) homology to at least one target mRNA expressed by a host, (b) two complementary RNA regions which are unrelated to any endogenous RNA in the host, and which are in proximity to (a), wherein the RNA, when introduced into the host, reduces the expression of the target mRNA or any substantially similar endogenous mRNA.

In an eighth embodiment, this invention concerns a recombinant construct comprising an RNA having:

(a) homology to at least one target mRNA expressed by a host, (b) an RNA region unrelated to any endogenous RNA in the host and located 5' to (a), and (c) the reverse complement of the RNA in (b) located 3' to (a), wherein the RNA, when introduced into the host, reduces the expression of the target mRNA or any substantially similar endogenous mRNA.

In a ninth embodiment, this invention concerns a recombinant construct comprising an RNA having:

(a) homology to at least one target mRNA expressed by the host, and (b) two complementary RNA regions which are unrelated to any endogenous RNA in the host, and which are located 5' to (a), wherein the RNA, when introduced into the host, reduces the expression of the target mRNA or any substantially similar endogenous mRNA.

In a tenth embodiment, this invention concerns a recombinant construct comprising an RNA having:

(a) homology to at least one target mRNA expressed by the host, and (b) two complementary RNA regions which are unrelated to any endogenous RNA in the host, and which are located 3' to (a), wherein the RNA, when introduced into the host, reduces the expression of the target mRNA or any substantially similar endogenous mRNA.

In an eleventh embodiment, this invention concerns a recombinant construct comprising an RNA having:

(a) homology to at least one target mRNA expressed by the host, and (b) two complementary RNA regions which are unrelated to any endogenous RNA in the host, and which are located within (a), wherein the RNA, when introduced into the host, reduces the expression of the target mRNA or any substantially similar endogenous mRNA.

In another aspect of any of the foregoing RNAs, the RNA region or regions which are unrelated to any endogenous RNA in the host comprise a synthetic, non-naturally occurring RNA sequence.

In still another aspect of any of the foregoing recombinant constructs, the RNA region or regions which are unrelated to any endogenous RNA in the host do not comprise plant viral RNA.

In a twelfth embodiment, this invention concerns a method for reducing expression of a target mRNA or any substantially similar endogenous mRNA which comprises:

(a) introducing into a host any of the above-described RNAs; and (b) selecting hosts which have reduced expression of the target mRNA or any substantially similar endogenous mRNA.

In a thirteenth embodiment this invention concerns, a recombinant construct comprising a promoter operably linked to a DNA sequence which, when expressed by a host produces an RNA having:

(a) homology to at least one target mRNA expressed by the host, (b) two complementary RNA regions which are encoded by any nucleic acid sequence in the genome of the host provided that said sequence does not encode the target mRNA or any sequence that is substantially similar to the target mRNA and said regions are in proximity to (a), wherein the expressed RNA reduces the expression of the target mRNA or any substantially similar endogenous mRNA.

In a fourteenth embodiment this invention concerns, a recombinant construct comprising a promoter operably linked to a DNA sequence which, when expressed by a host produces an RNA having:

(a) homology to at least one target mRNA expressed by the host, (b) an RNA region encoded by any nucleic acid sequence in the genome of the host provided that said sequence does not encode the target mRNA or any sequence that is substantially similar to the target mRNA and located 5' to (a), and (c) the reverse complement of the nucleic acid in (b) located 3' to (a), wherein the expressed RNA reduces the expression of the target mRNA or any substantially similar endogenous mRNA.

In a fifteenth embodiment this invention concerns, a recombinant construct comprising a promoter operably linked to a DNA sequence which, when expressed by a host produces an RNA having:

(a) homology to at least one target mRNA expressed by the host, and (b) two complementary RNA regions which are encoded by any nucleic acid sequence in the genome of the host provided that said sequence does not encode the target mRNA or any sequence that is substantially similar to the target mRNA, and which regions are located 5' to (a), wherein the expressed RNA reduces the expression of the target mRNA or any substantially similar endogenous mRNA.

In a sixteenth embodiment this invention concerns, a recombinant construct comprising a promoter operably linked to a DNA sequence which, when expressed by a host produces an RNA having:

(a) homology to at least one target mRNA expressed by the host, and (b) two complementary RNA regions which are encoded by any nucleic acid sequence in the genome of the host provided that said sequence does not encode the target mRNA or any sequence that is substantially similar to the target mRNA, and which regions are located 3' to (a), wherein the expressed RNA reduces the expression of the target mRNA or any substantially similar endogenous mRNA.

In a seventeenth embodiment this invention concerns, a recombinant construct comprising a promoter operably linked to a DNA sequence which, when expressed by a host produces an RNA having:

(a) homology to at least one target mRNA expressed by the host, and (b) two complementary RNA regions which are encoded by any nucleic acid sequence in the genome of the host provided that said sequence does not encode the target mRNA or any sequence that is substantially similar to the target mRNA, and which regions are located within (a), wherein the expressed RNA reduces the expression of the target mRNA or any substantially similar endogenous mRNA.

In another aspect of any of the foregoing recombinant constructs, the RNA region or regions which are unrelated to any endogenous RNA in the host comprise a synthetic, non-naturally occurring RNA sequence.

In still another aspect of any of the foregoing recombinant constructs, the RNA region or regions which are unrelated to any endogenous RNA in the host do not comprise plant viral RNA.

In an eighteenth embodiment this invention concerns, a method for reducing expression of a target mRNA or any substantially similar endogenous mRNA which comprises:

(a) transforming a host with any of the above-described recombinant constructs; and (b) selecting hosts which have reduced expression of the target mRNA or any substantially similar endogenous mRNA.

In a nineteenth embodiment this invention concerns an RNA comprising:

(a) homology to at least one target mRNA expressed by a host, (b) two complementary RNA regions which are encoded by any nucleic acid sequence in the genome of the host provided that said sequence does not encode the target mRNA or any sequence that is substantially similar to the target mRNA and which regions are in proximity to (a), wherein the RNA, when introduced into the host, reduces the expression of the target mRNA or any substantially similar endogenous mRNA.

In a twentieth embodiment this invention concerns an RNA comprising:

(a) homology to at least one target mRNA expressed by a host, (b) an RNA region encoded by any nucleic acid sequence in the genome of the host provided that said sequence does not encode the target mRNA or any sequence that is substantially similar to the target mRNA and is located 5' to (a), and (c) the reverse complement of the RNA in (b) located 3' to (a), wherein the RNA, when introduced into the host, reduces the expression of the target mRNA or any substantially similar endogenous mRNA.

In a twenty-first embodiment this invention concerns an RNA comprising:

(a) homology to at least one target mRNA expressed by the host, and (b) two complementary RNA regions which are encoded by any nucleic acid sequence in the genome of the host provided that said sequence does not encode the target mRNA or any sequence that is substantially similar to the target mRNA and which regions are located 5' to (a), wherein the RNA, when introduced into the host, reduces the expression of the target mRNA or any substantially similar endogenous mRNA.

In a twenty-second embodiment this invention concerns an RNA comprising:

(a) homology to at least one target mRNA expressed by the host, and (b) two complementary RNA regions which are encoded by any nucleic acid sequence in the genome of the host provided that said sequence does not encode the target mRNA or any sequence that is substantially similar to the target mRNA, and which regions are located 3' to (a), wherein the RNA, when introduced into the host, reduces the expression of the target mRNA or any substantially similar endogenous mRNA.

In a twenty-third embodiment this invention concerns an RNA comprising:

(a) homology to at least one target mRNA expressed by the host, and (b) two complementary RNA regions which are encoded by any nucleic acid sequence in the genome of the host provided that said sequence does not encode the target mRNA or any sequence that is substantially similar to the target mRNA, and which are located within (a), wherein the RNA, when introduced into the host, reduces the expression of the target mRNA or any substantially similar endogenous mRNA.

In another aspect of any of the foregoing RNAs, the RNA region or regions which are unrelated to any endogenous RNA in the host comprise a synthetic, non-naturally occurring RNA sequence.

In still another aspect of any of the foregoing recombinant constructs, the RNA region or regions which are unrelated to any endogenous RNA in the host do not comprise plant viral RNA.

In a twenty-fourth embodiment this invention concerns a method for reducing expression of a target mRNA or any substantially similar endogenous mRNA which comprises:

(a) introducing into a host any of the above-described RNAs; and (b) selecting hosts which have reduced expression of the target mRNA or any substantially similar endogenous mRNA.

In a twenty-fifth embodiment, this invention concerns a method for identifying or screening an essential plant gene which comprises:

(a) transforming a plant cell with a recombinant construct comprising a constitutive promoter wherein said construct is capable of reducing expression of an essential plant gene with a high degree of frequency;

(b) quantifying all transformed plant cells from step (a);

(c) quantifying all transformed plant cells from a control which does not reduce expression of an essential plant gene; and (d) comparing the quantification of transformed plant cells selected from step (b) with the quantification of transformed plants cells selected from step (c) wherein the quantification of transformed plants cells selected from step (c) should substantially exceed the quantification of transformed plant cells selected from step (b).

In a twenty-sixth embodiment, this invention concerns a method for identifying or screening an essential plant gene which comprises:

(a) transforming a plant cell with any of the recombinant constructs of the invention comprising a promoter operably linked to a DNA sequence and which further comprises a constitutive promoter which is capable of reducing expression of an essential plant gene with a high degree of frequency;

(b) quantifying all transformed plant cells from step (a);

(c) quantifying all transformed plant cells from a control which does not reduce expression of an essential plant gene; and (d) comparing the quantification of transformed plant cells selected from step (b) with the quantification of transformed plants cells selected from step (c) wherein the quantification of transformed plants cells selected from step (c) should substantially exceed the quantification of transformed plant cells selected from step (b).

BRIEF DESCRIPTION OF THE DRAWING AND SEQUENCE LISTINGS

The invention can be more fully understood from the following detailed description and the accompanying drawings and Sequence Listing which form a part of this application.

FIG. 1 depicts the results of chimerism in experiments on antisense, "classical co-suppression", and complementary region reduction of expression for the soybean gene Fad2, a fatty acid desaturase. Chimerism is a measure of the percentage of individuals isolated in individual transformed lines that exhibit the phenotype characteristic of the desired trait.

Figure 2:
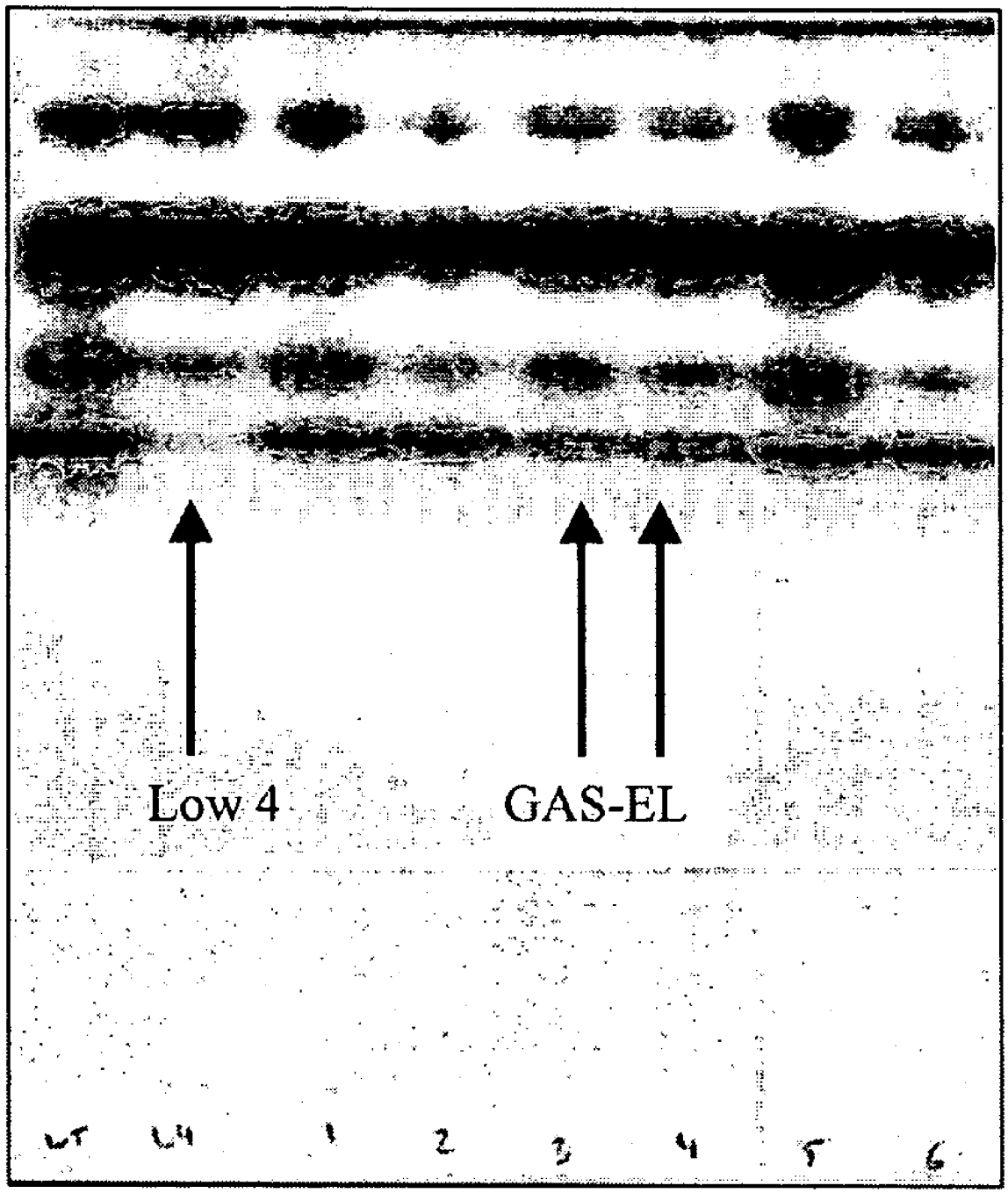

FIG. 2 shows total soybean sugars visualized after TLC separation. The raffinose and stachyose sugars are the lowest band in each lane. The "Low 4" lane is isolated from a soybean line known to have very low levels of raffinose/stachyose sugars. The two "GAS-EL" lines both have lower levels of raffinose/stachyose than are found in the surrounding lines indicating that the GAS1/GAS2 fragments contained within the EL construct are suppressing galactinol synthase activity in these lines.

The attached Sequence Listing (SEQ ID NOs:1-35) describe oligonucleotide sequences used in the design of various plasmids described herein, or the sequence of the complementary regions found in some of the plasmids.

SEQ ID NO:1 is the sequence of an oligonucleotide primer used in a polymerase chain reaction (PCR) amplification of the soybean Fad2-1 gene for insertion into plasmid pKS67 to produce plasmid pKS91.

SEQ ID NO:2 is the sequence of an oligonucleotide primer used in a PCR amplification of the soybean Fad2-1 gene for insertion into plasmid pKS67 to produce plasmid pKS91.

SEQ ID NO:3 is the sequence of an oligonucleotide primer used in a PCR amplification of the soybean Fad2-1 gene for insertion into plasmid pKS67 to produce plasmid pKS91.

SEQ ID NO:4 is the sequence of an oligonucleotide primer used in a PCR amplification of the soybean Fad2-1 gene for insertion into plasmid pKS67 to produce plasmid pKS91.

SEQ ID NO:5 is the sequence of an oligonucleotide primer used in a PCR amplification of the soybean Fad2-1 gene for insertion into plasmid pKS67 to produce plasmid pKS91.

SEQ ID NO:6 is the sequence of an oligonucleotide primer used in a PCR amplification of the soybean Fad2-1 gene for insertion into plasmid pKS67 to produce plasmid pKS91.

SEQ ID NO:7 is a linker oligonucleotide used to insert various restriction enzyme sites into the plasmid pKS17 to form the plasmid pKS102.

SEQ ID NO:8 is the sequence of an oligonucleotide primer used in a PCR amplification of the soybean Cer3 gene for insertion into plasmid pKS67 to form plasmid pKS100.

SEQ ID NO:9 is the sequence of an oligonucleotide primer used in a PCR amplification of the soybean Cer3 gene for insertion into plasmid pKS67 to form plasmid pKS100.

SEQ ID NO:10 is the sequence of an oligonucleotide primer used in a PCR amplification of the soybean Cer3 gene for insertion into plasmid pKS67 to form plasmid pKS100.

SEQ ID NO:11 is the sequence of an oligonucleotide primer used in a PCR amplification of the soybean Cer3 gene for insertion into plasmid pKS67 to form plasmid pKS100.

SEQ ID NO:12 represents the 1× complementary repeat designated ELVISLIVES found in plasmids pKS106 and pKS124.

SEQ ID NO:13 represents the 2× complementary repeat designated ELVISLIVES found in plasmids pKS133.

SEQ ID NO:14 is the sequence of an oligonucleotide primer used in a PCR amplification of the ELVISLIVES complementary region.

SEQ ID NO:15 is the sequence of an oligonucleotide primer used in a PCR amplification of the ELVISLIVES complementary region.

SEQ ID NO:16 is the sequence of an oligonucleotide primer used in a PCR amplification of the soybean Fad2-1 gene to produce the 599 nucleotide fragment inserted into plasmid pKS106 to produce the plasmid pKS111.

SEQ ID NO:17 is the sequence of an oligonucleotide primer used in a PCR amplification of the soybean Fad2-1 gene to produce the 599 nucleotide fragment inserted into plasmid pKS106 to produce the plasmid pKS111.

SEQ ID NO:18 is the sequence of the common 5' oligonucleotide primer used in a PCR amplification of the soybean Fad2-1 gene for use in testing size requirements for target sequences.

SEQ ID NO:19 is the sequence of a 3' oligonucleotide primer used in a PCR amplification of the soybean Fad2-1 gene for production of the 25 bp fragment.

SEQ ID NO:20 is the sequence of a 3' oligonucleotide primer used in a PCR amplification of the soybean Fad2-1 gene for production of the 75 bp fragment.

SEQ ID NO:21 is the sequence of a 3' oligonucleotide primer used in a PCR amplification of the soybean Fad2-1 gene for production of the 150 bp fragment.

SEQ ID NO:22 is the sequence of a 3' oligonucleotide primer used in a PCR amplification of the soybean Fad2-1 gene for production of the 300 bp fragment.

SEQ ID NO:23 is the sequence of a 3' oligonucleotide primer used in a PCR amplification of the soybean Fad2-1 gene for production of the 600 bp fragment.

SEQ ID NO:24 represents the 2× ELVISLIVES complementary repeat region from pBS68 which contains 2× ELVISLIVES complementary regions surrounding the 599 nucleotide Fad2-1 NotI fragment from pKS111 and a 969 nucleotide fragment from a soybean delta-9 desaturase.

SEQ ID NO:25 is the sequence of a 5' oligonucleotide primer used in a PCR amplification of the Lea promoter.

SEQ ID NO:26 is the sequence of a 3' oligonucleotide primer used in a PCR amplification of the Lea promoter.

SEQ ID NO:27 is the sequence of a 5' oligonucleotide primer used in a PCR amplification of the phaseolin 3'-end.

SEQ ID NO:28 is the sequence of a 3' oligonucleotide primer used in a PCR amplification of the phaseolin 3'-end.

SEQ ID NO:29 represents the 2× ELVISLIVES complementary repeat region from pKS149 that contains fragments from two soybean galactinol synthase genes GAS1 and GAS2 (411 and 435 nucleotides, respectively). The region is functionally attached to a late-soybean-embryo promoter (LEA) and a phaseolin 3' terminator region. This entire region is then cloned into the BamHI site of pKS136, which contains a 2× ELVISLIVES complementary repeat region controlled by a soybean Kti promoter and terminator region.

SEQ ID NO:30 represents the DNA sequence of the soybean galactinol synthase gene GAS1.

SEQ ID NO:31 represents the putative translation product DNA sequence of SEQ ID NO:30 the soybean galactinol synthase gene GAS1.

SEQ ID NO:32 represents the DNA sequence of the soybean galactinol synthase gene GAS2.

SEQ ID NO:33 represents the putative translation product DNA sequence of SEQ ID NO:32 the soybean galactinol synthase gene GAS2.

SEQ ID NO:34 represents the complementary region SHH3 from plasmid PHP17962, used in the construction of plasmid PHP17894 containing the phytoene desaturase fragment. The complementary regions are from 8-212 and 305-509, respectively. Restriction endonuclease sites for EcoRV, KpnI, KspI, SphI, and NcoI can be used as cloning sites between the complementary regions.

SEQ ID NO:35 represents the DNA sequence of the soybean acetolactate synthase (ALS) gene.

SEQ ID NO:36 is the sequence of a 3' oligonucleotide primer used in a PCR amplification of the soybean Fad2-1 gene for production of the 50 bp fragment.

DETAILED DESCRIPTION OF THE INVENTION

In the context of this disclosure, a number of terms shall be utilized.

The term "host" refers to any organism, or cell thereof, whether human or non-human into which a recombinant construct can be stably or transiently introduced in order to reduce gene expression.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for g or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS*. 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "essential plant genes" as used herein refers to genes encoding a product that is required for normal plant growth, development, and/or viability. In addition to ALS, examples of essential plant genes would include, but not be limited to, rate-limiting enzymes in amino acid, nucleic acid, or lipid biosynthesis. It is also believed that many genes with unknown function may be essential. Suppression of essential plant genes by chemical or genetic means will result in altered growth and/or development. If an essential gene is unique in the genome of the plant, suppression may lead to plant death, which is the basis of many plant herbicides.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225). The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al, (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "target mRNA" refers to any mRNA whose expression in the host is to be reduced.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al, (1987) *Nature* (*London*) 327:70-73; U.S. Pat. No. 4,945,050), or an *Agrobacterium*-mediated method using an appropriate Ti plasmid containing the transgene (Ishida Y. et al, 1996, Nature Biotech. 14:745-750).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

The terms "recombinant construct", "expression construct" and "recombinant expression construct" are used interchangeably herein. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al, (1985) *EMBO J.* 4:2411-2418; De Almeida et al, (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al (1998) *Plant Cell* 10:1747-1757).

Surprisingly and unexpectedly, it has been found that suitable nucleic acid sequences and their reverse complement can be used to alter the expression of any homologous, endogenous RNA (i.e., the target RNA) which is in proximity to the suitable nucleic acid sequence and its reverse complement. As is discussed below, the suitable nucleic acid sequence and its reverse complement can be either unrelated to any endogenous RNA in the host or can be encoded by any nucleic acid sequence in the genome of the host provided that nucleic acid sequence does not encode any target mRNA or any sequence that is substantially similar to the target mRNA.

Thus, the present invention presents a very efficient and robust approach to achieving single, or multiple, gene co-suppression using single plasmid transformation. As is discussed in greater detail below, the constructs are composed of promoters linked to mRNA(s) coding regions, or fragments thereof, that are targeted for suppression, and short complementary sequences that are unrelated to the targets. The complementary sequences can be oriented both 5', both 3', or on either side of the target sequence. The complementary sequences are preferred to be about 40-50 nucleotides in length, or more preferably 50-100 nucleotides in length, or most preferably at least or greater than 100-300 nucleotides. The complementary sequences are unrelated to the target, but can come from any other source. Preferred embodiments of these sequences include, but are not limited to, plant sequences, bacterial sequences, animal sequences, viral or phage sequences, or completely artificial, i.e. non-naturally occurring, sequences not known to occur in any organism (see "ELVISLIVES" below). All sequences can be compared to other known sequences, or each other, using any one of a number of sequence alignment programs as set forth below in Example 4.

The term "high degree of frequency" as used herein, with respect to the suppression efficiency, refers to the percentage of transformed lines that exhibit the target suppressed phenotype. High frequency percentages are expected to be in a range of at least 15-95% and any integer percentage found within the range. Preferred embodiments would include at least 15%, 20%, 25%, 30%, 35%, 40%, 45%, 50%, 55%, 60%, 65%, 70%, 75%, 80%, 85%, 90%, and 95%.

The present invention concerns a recombinant construct comprising a promoter operably linked to a DNA sequence which, when expressed by a host produces an RNA having:

(a) homology to at least one target mRNA expressed by the host, (b) two complementary RNA regions which are unrelated to any endogenous RNA in the host, and which are in proximity to (a), wherein the expressed RNA reduces the expression of the target mRNA or any substantially similar endogenous mRNA.

In another aspect the present invention concerns a recombinant construct comprising a promoter operably linked to a DNA sequence which, when expressed by a host produces an RNA having:

(a) homology to at least one target mRNA expressed by the host, (b) two complementary RNA regions which are encoded by any nucleic acid sequence in the genome of the host provided that said sequence does not encode the target mRNA or any sequence that is substantially similar to the target mRNA and said regions are in proximity to (a), wherein the expressed RNA reduces the expression of the target mRNA or any substantially similar endogenous mRNA.

Any promoter can be used to practice the invention. There can be mentioned a beta-conglycinin promoter, a Kunitz soybean Trypsin Inhibitor (KSTI or Kti) promoter, a Gly m Bd 28K promoter, T7 promoter, a 35S promoter and a beta-phaseolin promoter. The preferred promoter is that of the α'-subunit of beta-conglycinin (referred to herein as the beta-conglycinin promoter). Co-suppressed plants that contain recombinant expression constructs with the promoter of the α'-subunit of beta-conglycinin will often exhibit suppression of both the α and α' subunits of beta-congylcinin (as described in PCT Publication No. WO 97/47731, published on Dec. 18, 1997, the disclosure of which is hereby incorporated by reference). Particularly preferred promoters are those that allow seed-specific expression. This may be especially useful since seeds are the primary source consumable protein and oil, and also since seed-specific expression will avoid any potential deleterious effect in non-seed tissues.

Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al, (1984) *Ann. Rev. Plant Physiol.* 35:191-221; Goldberg et al, (1989) *Cell* 56:149-160). Moreover, different seed storage proteins may be expressed at different stages of seed development.

Expression of seed-specific genes has been studied in great detail (See reviews by Goldberg et al, (1989) *Cell* 56:149-160 and Higgins et al, (1984) *Ann. Rev. Plant Physiol.* 35:191-221). There are currently numerous examples of seed-specific expression of seed storage protein genes in transgenic dicotyledonous plants. These include genes from dicotyledonous plants for bean β-phaseolin (Sengupta-Gopalan et al, (1985) *Proc. Natl. Acad. Sci. USA* 82: 3320-3324; Hoffman et al, (1988) *Plant Mol. Biol.* 11: 717-729), bean lectin (Voelker et al, (1987) *EMBO J.* 6: 3571-3577), soybean lectin (Okamuro et al, (1986) *Proc. Natl. Acad. Sci. USA* 83: 8240-8244), soybean Kunitz trypsin inhibitor (Perez-Grau et al, (1989) *Plant Cell* 1: 095-1109), soybean b-conglycinin (Beachy et al, (1985) *EMBO J.* 4: 3047-3053; pea vicilin (Higgins et al, (1988) *Plant Mol. Biol.* 11:683-695), pea convicilin (Newbigin et al, (1990) *Planta* 180:461-470), pea legumin (Shirsat et al, (1989) *Mol. Gen. Genetics* 215:326-331); rapeseed napin (Radke et al, (1988) *Theor. Appl. Genet.* 75:685-694) as well as genes from monocotyledonous plants such as for maize 15 kD zein (Hoffman et al, (1987) *EMBO J.* 6:3213-3221), maize 18 kD oleosin (Lee at al., (1991) *Proc. Natl. Acad. Sci. USA* 88:6181-6185), barley β-hordein (Marris et al, (1988) *Plant Mol. Biol.* 10:359-366) and wheat glutenin (Colot et al, (1987) *EMBO J.* 6:3559-3564). Moreover, promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *Brassica napus* seeds (Vandekerckhove et al, (1989) *Bio/Technology* 7:929-932), bean lectin and bean β-phaseolin promoters to express luciferase (Riggs et al, (1989) *Plant Sci.* 63:47-57), and wheat glutenin promoters to express chloramphenicol acetyl transferase (Colot et al, (1987) *EMBO J.* 6:3559-3564).

As was noted above any type of promoter such as constitutive, tissue-preferred or inducible promoters can be used to practice the invention. Examples of constitutive promoters include the cauliflower mosaivirus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters that are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). In addition to those mentioned above, other examples of seed-specific promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95-102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21), 6426 (1990). See the following site relating to the waxy promoter: Kloesgen, R. B., Gierl, A., Schwarz-Sommer, Z. S. and Saedler, H., Molecular analysis of the waxy locus of *Zea mays, Mol. Gen. Genet.* 203, 237-244 (1986). Promoters that express in the embryo, pericarp, and endosperm are disclosed in PCT Application No. WO 00/11177 published Mar. 2, 2000, and PCT Application No. WO 00/12733 published Mar. 9, 2000. The disclosures each of these are incorporated herein by reference in their entirety.

Either heterologous or non-heterologous (i.e., endogenous) promoters can be used to practice the invention.

The promoter is then operably linked using conventional means well known to those skilled in the art to a DNA sequence which, when expressed by a host produces an RNA meeting certain criteria.

The host can be any organism, or cell thereof, into which the recombinant construct of this invention can be stably or transiently introduced in order to alter gene expression. Examples of suitable hosts include, but are not limited to, a plant, animal, protozoan, bacterium, virus or fungus. The plant may be a monocot, dicot or gymnosperm; the animal may be a vertebrate or invertebrate. Preferred microbes are those used in agriculture or by industry. Fungi include organisms in both the mold and yeast morphologies.

Plants include *Arabidopsis*; field crops (e.g., alfalfa, barley, bean, corn, cotton, flax, pea, rape, rice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, blackberry, blueberry, cacao, cherry, coconut, cranberry, date, fajoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); etc.

Examples of human or non-human vertebrate animals include mammals, fish, cattle, goat, pig, sheep, rodent, hamster, mouse, rat, guinea pigs, rabbits, and primate; invertebrate animals include nematodes, other worms, *Drosophila*, and other insects. Representative orders of insects include *Coleoptera, Diptera, Lepidoptera*, and *Homoptera*.

The DNA sequence expressed by the host produces an RNA having:

(a) homology to at least one target mRNA expressed by the host;

(b1) two complementary RNA regions which are unrelated to any endogenous RNA in the host, and which are in proximity to the target mRNA, wherein the expressed RNA reduces the expression of the target RNA or any substantially similar endogenous mRNA, or (b2) two complementary RNA regions which are encoded by any nucleic acid sequence in the genome of the host provided that said sequence does not encode the target mRNA or any sequence that is substantially similar to the target mRNA and said regions are in proximity to (a).

The complementary RNA regions may comprise any of the following:

(a) any nucleic acid sequence not normally present in the genome of a host, i.e, are not related to any endogenous RNA in the host; or (b) any nucleic acid sequence in the genome of the host which encodes the complementary regions provided that said sequence does not encode the target mRNA or any sequence that is substantially similar to the target mRNA.

With respect to (a) any nucleic acid sequence not normally present in the genome of a host, the RNA region or regions which are unrelated to any endogenous RNA in the host may comprise a synthetic, non-naturally occurring RNA sequence. In still a further aspect, these RNA region or regions, optionally, may or may not comprise plant viral RNA.

With respect to (b) any nucleic acid sequence in the genome of the host which encodes the complementary regions provided that said sequence does not encode the target mRNA or any sequence that is substantially similar to the target mRNA, this sequence comprises transcribed or non-transcribed nucleic acid sequences which may be present in the genome of the host, i.e., this sequence may or may not be expressed by the host.

The complementary RNA regions described herein are in proximity to the target mRNA. The term "in proximity" means that the complementary regions are operably linked 5' to the target mRNA, or 3' to the target mRNA, or within the target mRNA, or 5' and 3' to the target mRNA, i.e., the complementary regions or sequences can be found on either end of the target mRNA.

The complementary RNA regions can be any size that is suitable for altering the expression of the target mRNA. The complementary sequences are preferred to be about 40-50 nucleotides in length, or more preferably 50-100 nucleotides in length, or most preferably greater than 100-300 nucleotides. These complementary sequences can be synthesized using conventional means well known to those skilled in the art.

Examples of suitable complementary RNA regions which can be used to practice the invention include, but are not limited to, SEQ ID NO:12 and 13, bacterial sequences, jellyfish sequences, or any artificial or naturally occurring sequences.

In another embodiment this invention concerns a method for reducing expression of a target mRNA or any substantially similar endogenous mRNA which comprises:

(a) introducing into a host any of the recombinant constructs discussed herein, and (b) selecting hosts which have reduced expression of the target mRNA or any substantially similar endogenous mRNA.

Transformation methods are discussed above and are well known to those skilled in the art.

Selection of the host having the desired phenotype will depend upon the target mRNA whose expression is being altered. As was noted above, the target mRNA may be any mRNA whose expression in the host is to be altered. Typically, it should share homology with the RNA produced by the host transformed with a recombinant construct of the invention. The expression of more than one target mRNA may be reduced provided that these targets share homology with the RNA produced by the host transformed with a recombinant construct of the invention.

In still another embodiment, this invention concerns a recombinant construct comprising an RNA in lieu of a DNA sequence. Thus, this RNA comprises:

(a) homology to at least one target mRNA expressed by a host, (b) two complementary RNA regions which are unrelated to any endogenous RNA in the host, and which are in proximity to (a), wherein the RNA, when introduced into the host, reduces the expression of the target mRNA or any substantially similar endogenous mRNA.

In another aspect, this invention concerns a recombinant construct comprising an RNA in lieu of a DNA sequence in which the RNA comprises:

(a) homology to at least one target mRNA expressed by a host, (b) two complementary RNA regions which are encoded by any nucleic acid sequence in the genome of the host provided that said sequence does not encode the target mRNA or any sequence that is substantially similar to the target mRNA and which regions are in proximity to (a), wherein the RNA, when introduced into the host, reduces the expression of the target mRNA or any substantially similar endogenous mRNA.

As was discussed above the complementary RNA regions may comprise any of the following:

(a) any nucleic acid sequence not normally present in the genome of a host, i.e, are not related to any endogenous RNA in the host; or (b) any nucleic acid sequence in the genome of the host which encodes the complementary regions provided that said sequence does not encode the target mRNA or any sequence that is substantially similar to the target mRNA.

With respect to (a) any nucleic acid sequence not normally present in the genome of a host, the RNA region or regions which are unrelated to any endogenous RNA in the host may comprise a synthetic, non-naturally occurring RNA sequence. In still a further aspect, these RNA region or regions, optionally, may or may not comprise plant viral RNA.

With respect to (b) any nucleic acid sequence in the genome of the host which encodes the complementary regions provided that said sequence does not encode the target mRNA or any sequence that is substantially similar to the target mRNA, this sequence comprises transcribed or non-transcribed nucleic acid sequences which may be present in the genome of the host.

The complementary RNA regions described herein are in proximity to the target mRNA. The term "in proximity" means that the complementary regions are operably linked 5' to the target mRNA, or 3' to the target mRNA, or within the target mRNAS, or 5' and 3' to the target mRNA, i.e., the complementary regions or sequences can be found on either end of the target mRNA.

In addition, these RNAs can be used in a method for reducing expression of a target mRNA or any substantially similar endogenous mRNA which comprises:

(a) introducing into a host any of the RNAs described herein; and (b) selecting hosts which have reduced expression of the target mRNA or any substantially similar endogenous mRNA.

In still a further aspect, the present invention concerns a method for identifying or screening an essential plant gene which comprises:

(a) transforming a plant cell with a recombinant construct comprising a constitutive promoter wherein said construct is capable of reducing expression of an essential plant gene with a high degree of frequency;

(b) quantifying all transformed plant cells from step (a);

(c) quantifying all transformed plant cells from a control which does not reduce expression of an essential plant gene; and (d) comparing the quantification of transformed plant cells selected from step (b) with the quantification of transformed plants cells selected from step (c) wherein the quantification of transformed plants cells selected from step (c) should substantially exceed the quantification of transformed plant cells selected from step (b).

Any essential plant gene can be identified or screened using the method of the invention. An important aspect of this method is the use of a constitutive promoter and a recombinant construct capable of reducing expression of an essential plant gene with a high degree of frequency.

Essential plant genes are defined above.

Constitutive promoters are defined above. Preferably, the constitutive promoter is a high level or strong constitutive promoter wherein expression of the gene under the control of the promoter results in production of high levels of mRNA.

Any recombinant construct comprising a constitutive promoter which is capable of reducing expression of an essential plant gene with a high degree of frequency can be used to practice the invention. In a preferred embodiment, the recombinant construct can be any of the recombinant constructs of the invention comprising a promoter operably linked to a DNA sequence provided that the promoter is a constitutive promoter. The term high degree of frequency is defined above.

Any plant cells can be transformed using standard transformation methods as described above.

The number of plant cells transformed with a recombinant construct comprising a constitutive promoter wherein the recombinant construct is designed to reduce expression of an essential plant gene is quantified and compared to the number of plant cells transformed using a control in which expression of the essential plant gene is not reduced. If the number of plant cells transformed with the control substantially exceeds the number of plant cells transformed with the recombinant construct designed to reduce expression of an essential plant gene, then an essential plant gene has been identified/screened. By "substantially exceeds", it is meant at least a five-fold difference and, preferably, a ten-fold difference. Also preferred would be a 4-fold, 6-fold, 7-fold, 8-fold, 9-fold, or greater than a 10-fold difference. Thus, the number of plant cells transformed with the control should be at least five-fold greater than the number of plant cells transformed with the recombinant construct designed to reduce expression of an essential plant gene.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. The disclosures contained within the references used herein are hereby incorporated by reference.

Example 1

Transformation of Somatic Soybean Embryo Cultures

Generic Stable Soybean Transformation Protocol:

Soybean embryogenic suspension cultures are maintained in 35 ml liquid media (SB55 or SBP6) on a rotary shaker, 150 rpm, at 28° C. with mixed fluorescent and incandescent lights on a 16:8 h day/night schedule. Cultures are subcultured every four weeks by inoculating approximately 35 mg of tissue into 35 ml of liquid medium.

TABLE 1

Stock Solutions (g/L):

MS Sulfate 100X Stock

| | |
|---|---|
| $MgSO_4 7H_2O$ | 37.0 |
| $MnSO_4 H_2O$ | 1.69 |
| $ZnSO_4 7H_2O$ | 0.86 |
| $CuSO_4 5H_2O$ | 0.0025 |

MS Halides 100X Stock

| | |
|---|---|
| $CaCl_2 2H_2O$ | 44.0 |
| KI | 0.083 |
| $CoCl_2 6H_2O$ | 0.00125 |
| $KH_2PO_4$ | 17.0 |
| $H_3BO_3$ | 0.62 |
| $Na_2MoO_4 2H_2O$ | 0.025 |

MS FeEDTA 100X Stock

| | |
|---|---|
| $Na_2EDTA$ | 3.724 |
| $FeSO_4 7H_2O$ | 2.784 |

B5 Vitamin Stock

| | |
|---|---|
| 10 g | m-inositol |
| 100 mg | nicotinic acid |
| 100 mg | pyridoxine HCl |
| 1 g | thiamine |

SB55 (per Liter, pH 5.7)

| | |
|---|---|
| 10 ml | each MS stocks |
| 1 ml | B5 Vitamin stock |
| 0.8 g | $NH_4NO_3$ |
| 3.033 g | $KNO_3$ |
| 1 ml | 2,4-D (10 mg/mL stock) |
| 60 g | sucrose |
| 0.667 g | asparagine |

SBP6 same as SB55 except 0.5 ml 2,4-D

SB103 (per Liter, pH 5.7)

1X MS Salts
6% maltose
750 mg $MgCl_2$
0.2% Gelrite

SB71-1 (per Liter, pH 5.7)

1X B5 salts
1 ml B5 vitamin stock
3% sucrose
750 mg $MgCl_2$
0.2% Gelrite

Soybean embryogenic suspension cultures are transformed with pTC3 by the method of particle gun bombardment (Klein et al (1987) *Nature* 327:70). A DuPont Biolistic PDS1000/HE instrument (helium retrofit) is used for these transformations.

To 50 ml of a 60 mg/ml 1 µm gold particle suspension is added (in order); 5 µl DNA (1 µg/µl), 20 µl spermidine (0.1 M), and 50 µl $CaCl_2$ (2.5 M). The particle preparation is agitated for 3 min, spun in a microfuge for 10 sec and the supernatant removed. The DNA-coated particles are then washed once in 400 µl 70% ethanol and resuspended in 40 µl of anhydrous ethanol. The DNA/particle suspension is sonicated three times for 1 sec each. Five µl of the DNA-coated gold particles are then loaded on each macro carrier disk. For selection, a plasmid conferring resistance to hygromycin phosphotransferase (HPT) may be co-bombarded with the silencing construct of interest.

Approximately 300-400 mg of a four week old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1000 psi and the chamber is evacuated to a vacuum of 28 inches of mercury. The tissue is placed approximately 3.5 inches away from the retaining screen and bombarded three times. Following bombardment, the tissue is placed back into liquid and cultured as described above.

Eleven days post bombardment, the liquid media is exchanged with fresh SB55 containing 50 mg/ml hygromycin. The selective media is refreshed weekly. Seven weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Thus each new line is treated as an independent transformation event. These suspensions can then be maintained as suspensions of embryos maintained in an immature developmental stage or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in their fatty acid compositions (Example 3). Co-suppression of Fad2 results in a reduction of polyunsaturated fatty acids and an increase in oleic acid content.

It should be noted that any detectable phenotype, resulting from the co-suppression of a target gene, can be screened at this stage. This would include, but not be limited to, alterations in protein content, carbohydrate content, growth rate, viability, or the ability to develop normally into a soybean plant.

Example 2

Transformation of Maize

Generic Stable Maize Transformation Protocol:

Transformation of plasmid DNA in Hi-II strains of maize follows the standard Hi-II bombardment transformation protocol (Songstad D. D. et al, (1996) *In Vitro Cell Dev. Biol. Plant* 32:179-183). Cells are transformed by culturing maize immature embryos (approximately 1-1.5 mm in length) onto 560P medium containing N6 salts, Erikkson's vitamins, 0.69 g/l proline, 2 mg/l 2,4-D and 3% sucrose. After 4-5 days of incubation in the dark at 28° C., embryos are removed from 560P medium and cultured, scutellum up, onto 560Y medium which is equivalent to 560P but contains 12% sucrose. Embryos are allowed to acclimate to this medium for 3 h prior to transformation. The scutellar surface of the immature embryos is targeted using particle bombardment with either a mixture containing UBI:moPAT:pinII+UBI:GUS:pinII plasmids, or with a combination of these two plasmids plus any one of the constructs of the present invention (UBI is the ubiquitin-1 promoter, Christensen et al (1989) *Plant Mol Bio* 12:619-632; moPAT refers to a "monocot-optimized phosphinothricin acyltransferase" gene conferring resistance to the herbicide glufosinate ammonium, referenced in PCT Application No. WO 98/30701 published on Jul. 16, 1998; the pinII (proteinase inhibitor) terminator is described in An et al (1989) *Plant Cell* 1:115-122; and the GUS gene (beta-glucuronidase) is described in Jefferson et al (1986) *PNAS* 83:8447-8451). Embryos are transformed using the PDS-1000 Helium Gun from Bio-Rad at one shot per sample using 650PSI rupture disks. DNA delivered per shot averages about 0.1667 ug. An equal number of embryos per ear are bombarded with either the control DNA (PAT/GUS) or the mixture of control with any one of the constructs of the present invention. Following bombardment, all embryos are cultured and maintained on 560L medium (N6 salts, Eriksson's vitamins, 0.5 mg/l thiamine, 20 g/l sucrose, 1 mg/l 2,4-D, 2.88 g/l proline, 2.0 g/l gelrite, and 8.5 mg/l silver nitrate). After 2-7 days post-bombardment, all the embryos from both treatments are transferred onto N6-based medium containing 3 mg/l bialaphos Pioneer 560P medium described above, with no proline and with 3 mg/l bialaphos). Plates are maintained at 28° C. in the dark and are observed for colony recovery with transfers to fresh medium occurring every two weeks.

Transient Maize Assays:

High type II callus is maintained by subculturing onto fresh 560P medium every two weeks. Healthy callus is pushed through a 0.77 mm² nylon mesh and resuspended in MS culture medium with 2 mg/l 2,4-D at a density of 3 grams of tissue/40 ml medium. The cell suspension are then pipetted in 4 ml aliquots (each containing approximately 300 mg of cells) onto glass filter papers for bombardment using a vacuum apparatus. These filters are then placed on 560P medium and cultured in the dark at 26° C. After 2-4 days the filters are removed from the culture medium and excess liquid is removed using a vacuum apparatus. Filters with cells are then shot (using the DuPont Biolistics PDS1000/He gun) according to established methods (see example above) using 1 μm gold particles and 650 psi rupture disks. Immediately after bombardment filters are returned to 560P culture medium and cultured in the dark at 26° C. All DNA's are adjusted to obtain a final concentration of 1 μg/total DNA/particle prep tube (6 shots). The typical experiment is shot as follows:

GUS DNA+control DNA+Luciferase DNA

GUS DNA+silencing construct DNA+Luciferase DNA

Two days after bombardment cells are scraped from filters and protein is extracted, and enzyme activity is determined, using the luciferase assays outlined in the Dual-Luciferase Reporter Assay protocol (Promega Corp., Madison, Wis.). The same extract is also used to perform fluorometric GUS assays using the protocol of Rao and Flynn (1990) *Biotechniques* 8:38-40. Data presented in Example 8 below is plotted as the ratio of GUS/Luciferase units.

Example 3

The Phenotype of Transgenic Soybean Somatic Embryos is Predictive of Seed Phenotypes from Resultant Regenerated Plants Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α' subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis somatic soybean embryo system behaves very similarly to maturing zygotic soybean embryos in vivo, and is therefore a good and rapid model system for analyzing the phenotypic effects of modifying the expression of genes in the fatty acid biosynthesis pathway.

Most importantly, the model system is also predictive of the fatty acid composition of seeds from plants derived from transgenic embryos. This is illustrated with two different antisense constructs in two different types of experiment that were constructed following the protocols set forth in the PCT Publication Nos. WO 93/11245 and WO 94/11516. Liquid culture globular embryos were transformed with a chimeric gene comprising a soybean microsomal $\Delta^{15}$ desaturase as described in PCT Publication No. WO 93/11245 which was published on Jun. 10, 1993, the disclosure of which is hereby incorporated by reference (experiment 1) or a soybean microsomal $\Delta^{12}$ desaturase as described in PCT Publication No. WO 94/11516 which was published on May 26, 1994, the disclosure of which is hereby incorporated by reference (experiment 2). Both gene constructs were introduced in antisense orientation under the control of a seed-specific promoter (β-conglycinin promoter) and gave rise to mature embryos. The fatty acid content of mature somatic embryos from lines transformed with vector only (control) and the vector containing the antisense chimeric genes as well as of seeds of plants regenerated from them was determined.

One set of embryos from each line was analyzed for fatty acid content and another set of embryos from that same line was regenerated into plants. Fatty acid analysis of single embryos was determined either by direct trans-esterification of individual seeds in 0.5 mL of methanolic $H_2SO_4$ (2.5%) or by hexane extraction of bulk seed samples followed by trans-esterification of an aliquot in 0.8 mL of 1% sodium methoxide in methanol. Fatty acid methyl esters were extracted from the methanolic solutions into hexane after the addition of an equal volume of water. In all cases, if there was a reduced 18:3 content in a transgenic embryo line when compared to an untransformed control, then a corresponding reduction in 18:3 content was also observed in the segregating seeds of the plant derived from that transformed line (Table 2).

TABLE 2

Percent 18:3 Content Of Embryos and Seeds of Control and $\Delta^{15}$ Antisense Construct Transgenic Soybean Lines

| Transformant Line | Embryo Average (SD, n = 40) | Seed Average (SD, n = 10) |
|---|---|---|
| Control | 12.1 (2.6) | 8.9 (0.8) |
| $\Delta^{15}$ antisense, line 1 | 5.6 (1.2) | 4.3 (1.6) |
| $\Delta^{15}$ antisense, line 2 | 8.9 (2.2) | 2.5 (1.8) |
| $\Delta^{15}$ antisense, line 3 | 7.3 (1.1) | 4.9 (1.9) |
| $\Delta^{15}$ antisense, line 4 | 7.0 (1.9) | 2.4 (1.7) |
| $\Delta^{15}$ antisense, line 5 | 8.5 (1.9) | 4.5 (2.2) |
| $\Delta^{15}$ antisense, line 6 | 7.6 (1.6) | 4.6 (1.6) |

*[Seeds which were segregating with wild-type phenotype and without a copy of the transgene are not included in these averages]

In addition, different lines containing the same antisense construct, were used for fatty acid analysis in somatic embryos and for regeneration into plants. About 55% of the transformed embryo lines showed an increased 18:1 content when compared with control lines (Table 3). Soybean seeds, of plants regenerated from different somatic embryo lines containing the same antisense construct, had a similar frequency (53%) of high oleate transformants as the somatic embryos (Table 3). On occasion, an embryo line may be chimeric. That is, 10-70% of the embryos in a line may not contain the transgene. The remaining embryos that do contain the transgene, have been found in all cases to be clonal. In such a case, plants with both wild type and transgenic phenotypes may be regenerated from a single, transgenic line, even if most of the embryos analyzed from that line had a transgenic phenotype. An example of this is shown in Table 4, in which, of 5 plants regenerated from a single embryo line, 3 have a high oleic phenotype and two were wild type. In most cases, all the plants regenerated from a single transgenic line will have seeds containing the transgene. Thus, it was concluded that an altered fatty acid phenotype observed in a transgenic, mature somatic embryo line is predictive of an altered fatty acid composition of seeds of plants derived from that line.

TABLE 3

Oleate Levels in Somatic Embryos and Seeds of Regenerated Soybeans Transformed With, or Without, $\Delta^{12}$ Desaturase Antisense Construct

| | # of Vector Lines | # of Lines with High 18:1 | Average* %18:1 |
|---|---|---|---|
| Somatic embryos: | | | |
| Control | 19 | 0 | 12.0 |
| $\Delta^{12}$ antisense | 20 | 11 | 35.3 |
| Seeds of regenerated plants: | | | |
| Control | 6 | 0 | 18.2 |
| $\Delta^{12}$ antisense | 17 | 9 | 44.4 |

*average 18:1 of transgenics is the average of all embryos or seeds transformed with the $\Delta^{12}$ antisense construct in which at least one embryo or seed from that line had an 18:1 content greater than 2 standard deviations from the control value (12.0 in embryos, 18.2 in seeds). The control average is the average of embryos or seeds which do not contain any transgenic DNA but have been treated in an identical manner to the transgenics.

TABLE 4

Analysis of Seeds From Five Independent Plants Segregating From Plant Line 4

| Plant # | Average seed 18:1% | Highest seed 18:1% |
|---|---|---|
| 1 | 18.0 | 26.3 |
| 2 | 33.6 | 72.1 |
| 7 | 13.6 | 21.2 |
| 9 | 32.9 | 57.3 |
| 11 | 24.5 | 41.7 |

Mean of 15-20 seeds from 5 different plants regenerated from a single embryo line. Only plants # 2, 9 and 11 have seeds with a high 18:1 phenotype.

Example 4

Analysis of Nucleic Acid Sequences

Nucleic acid sequences comprising the target regions or the complementary regions are analyzed by conducting BLAST (Basic Local Alignment Search Tool; Altschul et al (1993) *J. Mol. Biol.* 215:403-410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The nucleic sequences are analyzed for similarity to all publicly available DNA sequences contained in the "nr" database using the BLASTN algorithm provided by the National Center for Biotechnology Information (NCBI). The DNA sequences can also be translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 5

A Comparison of Reduced Fad2 Expression Using Antisense vs. "Classical" Co-Suppression vs. "Complementary Region" Co-Suppression The following are some comparisons of antisense, "classical" co-suppression, and "complementary region" co-suppression (CRC) in similar experiments involving a soybean fatty acid desaturase (Fad). Fad2-1 is a gene locus encoding a Δ-12 desaturase from soybean that introduces a double bond into the oleic acid side-chain to form a polyunsaturated fatty acid. Reduction in the expression of Fad2-1 results in the accumulation of oleic acid (18:1, or an 18 carbon fatty acid tail with a single double bond) and a corresponding decrease in polyunsaturated fatty acid content.

The antisense constructs have all, or a portion, of the Fad2-1 coding region in a reverse orientation behind a strong promoter. It is believed that expression of the "antisense" RNA interferes with normal translation of the homologous endogenous gene via a hybridization event. The "classical" co-suppression construct have all, or a portion, of Fad2-1 in the normal sense orientation behind a strong promoter. It is believed that the expression of the "co-suppressing" RNA activates an uncharacterized mechanism that results in the partial, or total, elimination of the introduced RNA, as well as all RNAs having substantially similar sequences. The CRC construct used contains a portion of the Fad2-1 coding region (300 bp) duplicated in the reverse complement orientation, forming a complementary region specific for Fad2-1.

The plasmids used in these experiments were made using standard cloning methods well known to those skilled in the art (Sambrook et al (1989) *Molecular Cloning*, CSHL Press, New York). A starting plasmid pKS18HH (U.S. Pat. No. 5,846,784 the contents of which are hereby incorporated by reference) contains a hygromycin B phosphotransferase (HPT) obtained from *E. coli* strain W677 under the control of a T7 promoter and the 35S couliflower mosaic virus promoter. Plasmid pKS18HH thus contains the T7 promoter/HPT/T7 terminator cassette for expression of the HPT enzyme in certain strains of *E. coli*, such as NovaBlue (DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restiction endonuclease sites suitable for the cloning other chimeric genes into this vector. Plasmid ZBL100 (PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in PCT Application No. WO 94/11516, published on May 26, 1994). PKS91 is a derivative of pKS67 with a polymerase chain reaction (PCR) hairpin fragment of the soybean Fad2 gene inserted into the Not I site. The primers used in PCR reactions with soybean Fad2-1 DNA as follows (all sequences are 5' to 3'):

```
PCR(A)
GAATTCGCGGCCGCATGGGAGGTAGAGGTC        SEQ ID NO:1

GGAAAACCATGCAACCCATTGGTACTTGCT        SEQ ID NO:2

PCR(B)
AGCAAGTACCAATGGGTTGCATGGTTTTCC        SEQ ID NO:3

AGCAAGTACCAATGGATACTTGTTCCTGTA        SEQ ID NO:4

PCR(A/AS)
TACAGGAACAAGTATCCATTGGTACTTGCT        SEQ ID NO:5

GAATTCGCGGCCGCATGGGAGGTAGAGGTC        SEQ ID NO:6
```

The products of the three reactions (A)+(B)+(A/AS) are ligated together, digested with the restriction enzyme Not I, and the 1.3 kb fragment is cloned into the Not I site of KS67. The plasmid pKS91 was used in the experiments presented in this section. The 2.5 kb plasmid pKS17 contains pSP72 (obtained from Promega Biosystems) and the T7 promoter/HPT/T7 3' terminator region, and is the original vector into which the 3.2 kb BamHI-SalI fragment containing the 35S/HPT/NOS cassette was cloned to form pKS18HH. The plasmid pKS102 is a pKS17 derivative that is digested with XhoI and SalI, treated with mung-bean nuclease to generate blunt ends, and ligated to insert the following linker:

```
GGCGCGCCAAGCTTGGATCCGTCGACGGCGCGCC    SEQ ID NO:7
```

The plasmid pKS83 has the 2.3 kb BamHI fragment of ML70 containing the Kti3 promoter/NotI/Kti3 3' terminator region (described in PCT Application No. WO 94/11516, published on May 26, 1994) ligated into the BamHI site of pKS17. The plasmid pKS103 is a derivative of pKS83 with the 1.3 kb NotI fragment of pKS91 (containing the Fad2 complementary sequence) ligated into the NotI site.

In order to have comparable numbers of antisense lines to compare to the more numerous co-suppression constructs, it was necessary to include antisense experiments in which Fad 6 was co-bombarded with Fad 2-1. Fad6 is a gene encoding Δ-12 desaturase found in plastids (as opposed to Fad2 which is found in the microsomal compartment). It was believed that suppression of Fad2 and Fad6 simultaneously might give a stronger, or different, phenotype than Fad2 suppression alone. However, it has since been determined that Fad6 does not produce a phenotype, therefore the phenotypes obtained from antisense experiments with both Fad2 and Fad6 only reflect changes in Fad2-1 content.

Control embryos (286 individuals) had an average 18:1 content of 9% with a standard deviation (SD) of 6.2% (actual range 4-22%). Thus, an oleic acid content of 25% was chosen to represent a positive reduction in Fad2-1 which results in increased 18:1 that is more than 2 SDs from the mean, and higher than the highest control value seen. If a line has at least 1 embryo with an 18:1 content of 25% or more, it is counted as an antisense or a cosuppression event. Two experiments were combined to generate about 30 lines.

TABLE 5

Positive Transformed Lines With Reduced Fad2-1 Expression

| | Antisense | Co-suppression | CRC |
|---|---|---|---|
| Fad2-1 lines with >25% 18:1 content | 9 out of 31 | 9 out of 28 | 31 out of 33 |
| Percent total | 29% | 32% | 94% |

Another point to consider when analyzing transgenic plants with reduced expression due to antisense or co-suppression is chimerism. In the antisense and cosuppression experiments above the positive events lines detected may have only contained a single embryo out of ten with increased oleic acid content. Since all of these experiments had 10 embryos per line analyzed it is possible to graphically represent chimerism data by plotting actual embryo numbers against oleic content (greater or less than 25% which would be indicative of a tranformant reduced in Δ-12 expression). Therefore, if a line has little or no chimerism then all of its embryos will have a suppressed phenotype as opposed to being wild types. The data appear to be quite convincing that CRC (the grey box) transformants give consistently higher oleic acid contents with less chirmeric events:

Another issue is the efficiency with which a line exhibits the reduced expression phenotype. The results from the experiments here and in Example 6 confirm that the constructs containing the complementary regions in proximity to the target sequence were more effective at producing very high 18:1 content in embryos than either antisense or "classical" co-suppression (i.e. as opposed to complementary region containing co-suppression, CRC). The level of suppression achieved in an experiment is reflected in the corresponding increase of oleic acid content in the plants. The higher the average 18:1 content, the greater the degree of suppression. The complementary region containing constructs had oleic acid contents of 50% which is over 5 SDs from the control mean.

TABLE 6

Positive Transformed Lines With High Efficiency Reduction in Fad2-1 Expression

|  | Antisense | Co-suppression | CRC |
| --- | --- | --- | --- |
| Fad2-1 lines with >50% 18:1 content | 1 out of 31 | 3 out of 28 | 29 out of 33 |
| Percent total | 3% | 11% | 88% |

It appears that CRC is the most efficient and effective way of producing high 18:1 content in embryos with reduced Fad2-1 content. As was shown in Example 3 there is a phenotypic correlation between embryo oleic acid content and seed oleic acid content in transgenic plant. Thus experiments yielding embryonic lines with greater than 51% are most desirable since they appear to guarantee a seed oleic of greater than 80%:

It is noted that most positive seed lines detected are close to (or greater than) 80% oleic. Those few that aren't appear to be derived from embryo lines with a maximum oleic content ranging from 30% to 50%. To date no lines having a positive phenotype that had maximum embryo content of oleic acid less than 30%, and lines in the production system with 51% or more oleic acid content have always given rise to the best seed phenotypes. Additionally, the top five embryo lines from production (all greater than 50% oleic) gave the best phenotype in seed (greater than 80%) and the bottom four embryo lines (all less than 50% oleic in embryos) all gave less than 80% oleic acid content in seed.

Example 6

Target and Complementary Sequences can Both Co-Suppress their Endogenous Homologs The inclusion of a complementary region into the target region of a co-suppression construct results in the improvement of efficiency and uniformity in the resultant transformants (Example 5). The next step is to test if more than one gene can be suppressed using this approach. Preliminary results using a 300 nucleotide complementary region from Fad2-1 surrounding a 600 nucleotide target from the soybean thioesterase gene results in the suppression of both genes. This result was interesting for two reasons. First the complementary region from Fad2 was interrupted with thioesterase sequence, unlike the construct presented in Example 5. Second, the non-complementary target sequence (thioesterase) was inhibited in all lines that exhibited Fad2 reduction of expression, implying that there was equal efficiency of target and complementary region reduction of expression.

To further test if any target sequence expression can be efficiently repressed with any complementary region a construct was made using Fad2-1 as the target in combination with a complementary region from the soybean eceriferum3 (cer3) locus. Cer3 encodes one of 21 gene products known to be involved in wax biosynthesis in *Arabidopsis thaliana* (Hannoufa et al (1996) *Plant J* 10:459-67). The inhibition of a single cer3 gene has no visible phenotype in soybean. Also, cer3 is involved in a biosynthetic pathway that has no known interactions with the fatty acid metabolic pathway containing Fad2 activity. The plasmid pKS100 is a derivative of pKS67. PCR reactions are run with the following primers (5'-3' orientations) and cer3 DNA:

```
PCR(A + B)
GAATTCGCGGCCGCGGCACGAGATTTGAGG      SEQ ID NO:8

TTGCCCAATGTTTATGCATATGTAGAACTG      SEQ ID NO:9

PCR(A/AS)
CAGTTCTACATATGCATAAACATTGGGCAA      SEQ ID NO:10

GAATTCGCGGCCGCGGCACGAGATTTGAGG      SEQ ID NO:11
```

The product of the two reactions are ligated together, digested with NotI, and cloned into the NotI site of pKS67. Next, the 516 bp ScaI fragment from soybean Fad2-1 is ligated into a FspI digested pKS100 (within the Cer3 DNA, removing a small portion of the complementary sequence) to form pBS58. Restriction enzyme digestions were used to select the plasmid containing the Fad2 fragment in the sense or antisense orientation. It is believed that Fad2 expression is reduced efficiently in all constructs tested in soybeans.

Example 7

Suppression in Soybean of Fad2 by ELVISLIVES Complementary Region

Constructs have now been made which have "synthetic complementary regions" (SCR). Since the Fad 2 CR/TE2 target suppressed both endogenous genes in the one line examined, and since Cer3/Fad2 constructs suppress Fad2, it was deduced that it may be possible to use any complementary sequence to reduce the expression of a target. In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and 133 plasmids use the Kti promoter, both of these promoters exhibit strong tissue specific expression in the seeds of soybean. pKS106 uses a 3' termination region from the phaseolin gene, and pKS124 and 133 use a Kti 3' termination region. pKS106 and 124 have single copies of the 36 nucleotide EagI-ELVISLIVES sequence surrounding a NotI site (the amino acids given in parentheses are back-translated from the complementary strand): SEQ ID NO:12.

```
EagI    E   L   V   I   S   L   I   V   E   S   NotI
CGGCCG GAG CTG GTC ATC TCG CTC ATC GTC GAG TCG
                                              GCGGCCGC (S) (E) (V) (I) (L) (S) (I) (V) (L) (E) EagI
CGA CTC GAC GAT GAG CGA GAT GAC CAG CTC CGGCCG
``` pKS133 has 2× copies of ELVISLIVES surrounding the NotI site: SEQ ID NO:13

```
 EagI  E  L  V  I  S  L  I  V  E  S     EagI     E  L  V  I  S
cggccggagctggtcatctcgctcatcgtcgagtcg gcggccg gagctggtcatctcg L  I  V  E  S     NotI   (S) (E (V) (I) (L) (S) (I) (V) (L) (E)    EagI
ctcatcgtcgagtcg gcggccgc cgactcgacgatgagcgagatgaccagctc cggccgc (S)(E)(V)(I)(L)(S)(I)(V)(L)(E)  EagI
cgactcgacgatgagcgagatgaccagctc cggccg
```

The idea is that the single EL linker (SCR) can be duplicated to increase stem lengths in increments of approximately 40 nucleotides. A series of vectors will cover the SCR lengths between 40 bp and the 300 bp. Various target gene lengths are also under evaluation. It is believed that certain combinations of target lengths and complementary region lengths will give optimum suppression of the target, although preliminary results would indicate that the suppression phenomenon works well over a wide range of sizes and sequences. It is also believed that the lengths and ratios providing optimum suppression may vary somewhat given different target sequences and/or complementary regions.

The plasmid pKS106 is made by putting the EagI fragment of ELVISLIVES (SEQ ID NO:12) into the NotI site of pKS67. The ELVISLIVES fragment is made by PCR using two primers and no other DNA:

```
5'-GAATTCCGGCCGGAGCTGGTCATCTCGCTCATCG   SEQ ID NO:14
TCGAGTCGGCGGCCGCCGACTCGACGATGAGCGAGAT
GACCAGCTCCGGCCGGAATTC-3'

5'-GAATTCCGGCCGGAG-3'                   SEQ ID NO:15
```

The product of the PCR reaction is digested with EagI (5'-CGGCCG-3') and then ligated into NotI digested pKS67. The pKS111 is made by inserting a 599 nucleotide fragment from the delta-12 desaturase gene (Fad2, nucleotides 399-997), in an antisense orientation into the NotI site of pKS106. The Fad2 fragment is made by PCR using the following primers and Fad2 DNA as a template:

```
GAATTCGCGGCCGCTGAGTGATTGCTCACGAGT   SEQ ID NO:16

GAATTCGCGGCCGCTTAATCTCTGTCCATAGTT   SEQ ID NO:17
```

The PCR product is digested with NotI (5'-GCGGCCGC-3') and ligated into NotI digested pKS106. The total length of complementary sequence is 47 nucleotides (with the 8 nucleotides from the NotI site and 3 additional flanking bases). Co-suppression of Fad2 results in a decrease in the production of polyunsaturated fatty acids, and a corresponding increase in the accumulation of oleic acid (18:1) in soybeans. (see Example 3 above). Oleic acid concentrations in 18 of the 22 lines transformed with pKS111 were 2-5 times that found for the vector only controls, indicating co-suppression in 82% of the recovered transgenic plants. It appears that the placement of a single SCR (ELVISLIVES or EL) surrounding a short segment of Fad2 (600 bp) is sufficient to give co-suppression at efficiencies equal to the efficiencies achieved using the CRC constructs of Example 5. The term "ELVISLIVES" and "EL" are used interchangeably herein.

Additional plasmids can be used to test this example. For example, pKS121 contains the Kti3 promoter/NotI/Kti3 3' terminator fragment analogous to pKS83 inserted into the BamHI-SalI digested pKS102. The EagI digested ELVISLIVES cloning site made from SEQ ID NOs:14 and 15 is inserted into the NotI site of pKS121 to form pKS124. The Fad2 fragment from pKS111 is ligated into NotI digested pKS124 to form pKS132. The EagI digested EL PCR product can be ligated into NotI digested pKS124 to form the 2×EL pKS133. An additional 2×EL vector, pKS151, is similar to pKS133 except for the addition of a second hygromycin phosphotransferase gene with a 35S-CaMV promoter. Any synthetic sequence, or naturally occurring sequence, can be used in an analogous manner. The addition of the 599 bp soybean Fad2 fragment from pKS111 into a NotI digested pKS133 produces pKS136.

The efficiency of Fad2 suppression using 1×EL (pKS132) was compared to Fad2 suppression using the 2×EL (pKS136) construct. Hygromycin resistant lines of soybean embryos were isolated from independent transformation experiments with pKS132 and pKS136. Out of 98 lines containing pKS132, 69% displayed the high oleic phenotype. Out of 54 lines containing pKS136, 70% displayed the high oleic acid phenotype. Thus, both 1× and 2×EL constructs efficiently suppressed the Fad2 target gene.

Example 8

Length of the Fad2 Target Sequence Affects Suppression Efficiency

The length of the target was tested to determine the effect on the efficiency of suppression in an EL construct. PCR reactions were performed using the primers shown in Table 7 to create 25, 50, 75, 150, 300, and 600 fragments of Fad2 to place between 2EL complementary regions. The PCR products were cut with Not I and ligated into pBluescript and the sequence of the fragments was verified. Not I digested fragments were then ligated into the NotI of pKS151.

TABLE 7

Primers for PCR of Soybean Fad2

| Primer Sequence | Length | SEQ ID NO |
|---|---|---|
| 5'-GAATTCGCGGCCGCCCAATCTATTGGGTTCTC-3'<br>common 5'-end primer position 363 in Fad2 sequence | — | 18 |

TABLE 7-continued

Primers for PCR of Soybean Fad2

| Primer Sequence | Length | SEQ ID NO |
|---|---|---|
| 5'-GAATTCGCGGCCGCAACCTTGGAGAACCCAAT-3<br>3'-end primer for 25 bp fragment from 363-387 of Fad2 | 25 | 19 |
| 5'-GAATTCGCGGCCGCATCACCCACACACCAGTG-3'<br>3'-end primer for 50 bp fragment from 363-412 of Fad2 | 50 | 36 |
| 5'-GAATTCGCGGCCGCGGCATGGTGACCACACTC-3'<br>3'-end primer for 75 bp fragment from 363-437 of Fad2 | 75 | 20 |
| 5'-GAATTCGCGGCCGCTGAGAAATAAGGGACTAA-3'<br>3'-end primer for 150 bp fragment from 363-512 of Fad2 | 150 | 21 |
| 5'-GAATTCGCGGCCGCGAGTGTGACGAGAAGAGA-3'<br>3'-end primer for 300 bp fragment from 363-662 of Fad2 | 300 | 22 |
| 5'-GAATTCGCGGCCGCTTCTGATGAATCGTAATG-3'<br>3'-end primer for 600 bp fragment from 363-962 of Fad2 | 600 | 23 |

TABLE 8

Effect of Target Length on Suppression by 2XEL

| Fad2 Target Length | # Lines Tested | High Oleic |
|---|---|---|
| 25 | 8 | 0% |
| 50 | 8 | 0% |
| 75 | 8 | 13% |
| 150 | 8 | 13% |
| 300 | 29 | 34% |
| 600 | 20 | 60% |

The results in Table 8 show a clear correlation between target length and efficiency of suppression. The longest (600 bp) fragment of Fad2 is nearly twice as likely to be suppressed in the EL construct than a 300 bp fragment, while 50 bp and shorter fragments are not effective.

Example 9

Multiple Target Sequences can be Suppressed by 2×EL

A construct was assembled to test whether multiple target sequences can be used between EL complementary sequences to achieve simultaneous suppression. A 969 bp fragment from a soybean delta-9 desaturase was inserted into pKS136 next to the 599 bp Fad2 fragment to form pBS68. Both desaturase fragments were flanked by 2×EL complementary regions (2×EL-Fad2-Delta 9-2×EL the sequence of which is shown in SEQ ID NO:24).

Delta-9 desaturase catalyzes the double-bond at the 9-position of 18-carbon fatty acids to form oleic acid (18:1) from stearic acid (18:0), analogous to the delta-12 Fad2 which catalyzes the 12-position double bond that converts oleic acid to linoleic acid (18:2). Suppression of the unique Fad2 gene results in an accumulation of oleic acid at the expense of polyunsaturated fatty acids. Suppression of delta-9 desaturases results in an accumulation of stearic acid at the expense of all unsaturated fatty acids. However, there are several delta-9 desaturases in soybean (at least three) so it is unclear how the suppression of one member would affect oil composition. Transformation protocols and oil composition analyses were performed as previously outlined in Examples 1 and 3, respectively.

Transformation of soybean with pBS68 resulted in 113 hygromycin resistant lines. Of these 72 showed some oil phenotype (64%). The phenotypes of the 72 suppressed lines were: 18 were high stearate, 23 were high oleate, and 31 were both high oleate and high stearate. Therefore, multiple targets can be efficiently suppressed by a single EL construct.

Example 10

Suppression of Soybean Galactinol Synthase Genes in ELVISLIVES Constructs

Raffinose saccharides are a group of D-galactose-containing oligosaccharide derivatives of sucrose that are widely distributed in plants. Raffinose saccharides are characterized by the general formula: [O-β-D-galactopyranosyl-(1→6)$_n$-α-glucopyranosyl-(1→2)-β-D-fructofuranoside where n=0 through n=4 are known respectively as sucrose, raffinose, stachyose, verbascose, and ajugose.

Although abundant in many species, raffinose saccharides are an obstacle to the efficient utilization of some economically-important crop species. Raffinose saccharides are not digested directly by animals, primarily because alpha-galactosidase is not present in the intestinal mucosa [Gitzelmann et al (1965) *Pediatrics* 36:231-236; Rutloff et al (1967) *Nahrung* 11:39-46]. However, microflora in the lower gut are readily able to ferment the raffinose saccharides resulting in an acidification of the gut and production of carbon dioxide, methane and hydrogen gases [Murphy et al (1972) *J Agr. Food Chem.* 20:813-817; Cristofaro et al (1974) in Sugars in Nutrition, H. L. Sipple and K. W. McNutt, Eds. Academic Press, New York, Chap. 20, 313-335; Reddy et al (1980) *J Food Science* 45:1161-1164]. The resulting flatulence can severely limit the use of leguminous plants in animal, particularly human, diets. It is unfortunate that the presence of raffinose saccharides restricts the use of legumes in human diets because many of these species are otherwise excellent sources of protein and soluble fiber. Varieties of edible beans free of raffinose saccharides would be more valuable for human and animal diets and would facilitate broader access to the desirable nutritional qualities of edible leguminous plants.

The biosynthesis of raffinose saccharides has been well characterized [see Dey (1985) in Biochemistry of Storage Carbohydrates in Green Plants, P. M. Dey and R. A. Dixon, Eds. Academic Press, London, pp. 53-129]. The committed reaction of raffinose saccharide biosynthesis involves the synthesis of galactinol from UDP-galactose and myo-inositol. The enzyme that catalyzes this reaction is galactinol synthase (inositol 1-alpha-galactosyltransferase; EC 2.4.1.123). Synthesis of raffinose and higher homologues in the raffinose saccharide family from sucrose is thought to be catalyzed by distinct galactosyltransferases (for example, raffinose synthase and stachyose synthase). Studies in many species suggest that galactinol synthase is the key enzyme controlling the flux of reduced carbon into the biosynthesis of raffinose saccharides [Handley et al (1983) *J. Amer. Soc. Hort. Sci.* 108: 600-605; Saravitz, et al (1987) *Plant Physiol.* 83:185-189]. Altering the activity of galactinol synthase, either as a result of overexpression or through antisense inhibition, would change the amount of raffinose saccharides produced in a given tissue.

Related galactinol synthase genes already known in the art include sequences disclosed in U.S. Pat. Nos. 5,773,699 and 5,648,210, Kerr et al, "Nucleotide Sequences of Galactinol Synthase from Zucchini and Soybean" and Sprenger and Keller (2000) *Plant J* 21:249-258. Presumably related sequences are also disclosed in PCT Publication No. WO 98/50553, Lightner, "Corn Glycogenin". Two genes encoding soybean galactinol synthases have been previously identified (SEQ ID NOs:30 and 32, with the predicted translation products shown in SEQ ID NOs:31 and 33; presented in U.S. Pat No. U.S. Provisional Application No. 60/196,550, filed Apr. 11, 2000). Unlike the unique soybean Fad2 gene, it is known that there are multiple galactinol synthase genes in soybean. Because there are multiple genes encoding galactinol synthases, it is believed that suppression of more than one gene may be required to detect an effect on raffinose sugar levels.

A plasmid construct was assembled containing fragments of two galactinol synthase soybean genes Gas1 (390 bp from 13-402 of SEQ ID NO:30) and Gas2 (399 bp, from 129-527 of SEQ ID NO:32) cloned in the NotI site of a 2×EL cassette. The promoter region was a late embryo promoter (Lea) from soybean. The Lea promoter (Lee et al (1992) *Plant Physiol* 100:2121-2122; Genbank Accession No. M97285) was amplified from genomic A2872 soybean DNA with the following primers:

```
SEQ ID NO:25    5'-ATT AAC CTC AAT TCT TCT AAG
                (position 25-45 of M97285)

SEQ ID NO:26    5'-TTC AAA GAT CAA TTA TTT CC
                (position 995-1112 M97285)
``` and a phaseolin 3'-end (amplified with primers shown in SEQ ID NOs:27 and 28) was added. The entire Lea promoter -2×EL-Gas1-Gas2-2×EL-phaseolin 3'-end cassette was then cloned into the BamHI site of pKS136 to create the pKS149 vector (the sequence of the complete EL region of pKS149 is shown in SEQ ID NO:29). When introduced into plants pKS136 will inhibit both Fad2 (controlled by the Kti promoter) and Gas genes (controlled by the Lea promoter). Since the Kti promoter is active in embryos, it is possible to screen the embryos for high oleic phenotype, as described in the previous examples. Of the 119 lines isolated as hygromycin resistant 65% were found to have a high oleic phenotype.

These suppressed lines should also contain the Gas suppression cassette, allowing for the assay of raffinose sugars in the seedlings (Lea is not active during the early embryo stage). Raffinose sugars (galactinol, raffinose, stachyose, etc.) can be detected using thin layer chromatography. Plant samples are extracted with hexane then dried. The dried material is then resuspended in 80% methanol, incubated at room temperature for 1-2 hours, centrifuged, and 1-2 microliters of the supernatant is spotted onto a TLC plate (Kieselgel 60 CF, from EM Scientific, Gibbstown, N.J.; catalog no. 13749-6). The TLC is run in ethylacetate:isopropanol:20% acetic acid (3:4:4) for 1-1.5 hours. The air dried plates are sprayed with 2% sulfuric acid and heated until the charred sugars are detected. As shown in FIG. 2 the two lines labeled GAS-EL show reduced levels of raffinose sugars (lowest band) when compared to a control known to have very low raffinose sugars (Low 4). It is estimated that there is a 60% reduction of raffinose sugars in these lines when compared to wild-type soybean.

Example 11

ELVISLIVES Constructs can be Used to Screen Essential Plant Genes

Acetolactate synthase (ALS), also known as acetohydroxyacid synthase (AHAS), catalyzes the first common step in the biosynthesis of the branched chain amino acids isoleucine, leucine, and valine (Keeler et al, *Plant Physiol* 1993 102: 1009-18). Inhibition of native plant ALS by several classes of structurally unrelated herbicides including sulfonylureas, imidazolinones, and triazolopyrimidines, is lethal (Chong C K, Choi J D *Biochem Biophys Res Commun* 2000 279:462-7). Hence suppression of the gene encoding ALS in soybean should also be lethal. Thus, a well-validated herbicide target like ALS can inserted into EL vectors to test whether the transformation screening process can be used to identify essential plant genes. If so, other essential plant genes could be screened in a high-throughput method to identify novel potential herbicide targets. The term "essential plant genes" as used herein refers to genes encoding a product that is required for normal plant growth, development, and/or viability. In addition to ALS, examples of essential plant genes would include, but not be limited to, rate-limiting enzymes in amino acid, nucleic acid, or lipid biosynthesis. It is also believed that many genes with unknown function may be essential.

If a soy EL-ALS-EL construct is expressed during selection on hygromycin, very few events should be recovered, even though the HPT gene is present. If the EL-ALS-EL transcriptional unit is not expressed until late embryogenesis then recovery of transformation events should be similar in number to events obtained with vector controls, containing only the HPT gene. Constitutive expression of EL-ALS-EL can be accomplished by using a 35S promoter (pKS161). Expression of EL-ALS-EL restricted to late embryogenesis/germination can be accomplished with the previously described LEA promoter (pKS163).

To make KS161 the EL linker (SEQ ID NO:12) was cloned into the NotI site of pKS50 to produce pKS137 (a single EL complementary region with a 1 kb 35S CaMV promoter and a 700 bp nos 3'-end on a plasmid with 2 HPT genes one with a T7 promoter and the second with a 35S promoter). A 208 bp Hind III/EcoR I fragment from a soybean ALS gene (SEQ ID NO:35, fragment is from position 891-1114) was then cloned into the Hind III/EcoR I sites of pKS137 to produce pKS161. To make pKS163 the EL linker (SEQ ID NO:12) was cloned into the NotI site of pKS127 to produce KS139 (a single EL complementary region with the Lea promoter and the phaseolin 3'-end from Example 10 on a plasmid with 2 HPT genes one with a T7 promoter and the second with a 35S promoter). The 208 bp Hind III/EcoR I fragment from soybean ALS gene (SEQ ID NO:35, the HindIII/EcoRI fragment is from position 896-1103) was then cloned into the Hind III/EcoR I sites of KS139 to produce KS163.

KS161 and KS163 were transformed into 821 tissue (Example 1). The transformation efficiency for this tissue is normally in the range of 200-500 clones/gram of tissue. The results of two separate transformation experiments with KS161 and KS163, 4 weeks after bombardment and transfer to hygromycin-containing medium are:

| Expt. 1 | |
|---|---|
| KS161 (35S ALS EL) | 16 clones/gram tissue |
| KS163 (LEA ALS EL) | 247 clones/gram tissue |
| Expt. 2 | |
| KS161 (35S ALS EL) | 43 clones/gram tissue |
| KS163 (LEA ALS EL) | 467 clones/gram tissue |

In both experiments the 35S EL-ALS vector resulted in a >90% decrease in clone numbers, presumably because of suppression of the endogenous ALS gene throughout embryo formation stages. Therefore, the difference in clone numbers obtained for a novel gene fragment inserted into a 35S-EL construct (KS137) and a LEA-EL construct (KS139) can be used as a measure of whether the corresponding endogenous gene is essential or not, and thus whether or not it is a potential herbicide target. The effect of an unknown gene fragment on transformation efficiency can be measured within a few weeks of particle bombardment and thus this is a rapid means of identifying new herbicide target candidates. A typical screen consists of bombarding tissue with KS137 and KS139 as empty-vector controls, KS161 as a positive (ALS) control and various gene fragments, amplified by PCR to contain Hind III and EcoR I sites, cloned into the HindIII/EcoRI sites of KS137 and KS139.

The improved frequency of suppression achieved with the EL constructs allows for the possibility of a reliable screening method. A significant percentage of the hygromycin recovered transformation events must be suppressed by the target sequence contained within pKS137 or pKS139 in order for there to be a statistically definitive difference between the two experiments. The term "high degree of frequency" as used herein, with respect to the suppression efficiency, refers to the percentage of transformed lines that exhibit the target suppressed phenotype. High frequency percentages are expected to be in a range of at least 15-95% and any integer percentage found within the range. Preferred embodiments would include at least 15%, 20%, 25%, 30%, 35%, 40%, 45%, 50%, 55%, 60%, 65%, 70%, 75%, 80%, 85%, 90%, and 95%.

Example 12

Suppression of Cellulose Synthase in Maize Using EL Constructs

Cellulose synthase genes encode a family of proteins involved in cellulose formation in plants (Pear, et al, *Proc. Natl. Acad. Sci.* (USA) 93, 12637-12642; Saxena, et al, (1990), *Plant Molecular Biology* 15, 673-684). Several maize genes encoding cellulose synthases (cesA) have been recently cloned and characterized (PCT Publication No. WO 00/09706, published on Feb. 24, 2000). Fragments from four of these genes, cesA1, cesA4, cesA5, and cesA8, were used to test whether 1×EL could direct the suppression of these genes in maize.

One kb fragments from the 5'-end of the cDNA clones (including 5'-UTR and ORF sequences) for cesA1, cesA4, cesA5, and cesA8 were each cloned separately into the internal NotI site of 1×EL (SEQ ID NO:12) constructs. Each of these "EL-cesA-EL" cassettes was inserted into a plasmid containing a f3.7 promoter (a weak constitutive promoter exhibiting some preference for stalk-specific expression), a proteinase inhibitor 3'-end (pinII from potato, An et al (1989) *Plant Cell* 1: 115-122), and a 35S:BAR:pinII selection marker. A control plasmid containing an IN2 promoter driving a GUS gene with a pinII 3'-end was also made.

Results from maize transformation experiments with each of the constructs are shown in Table 9. Twenty-five lines were isolated for each of the four cesA gene constructs and 18 lines were isolated for the control. The height of the plants and stalk diameter were on average smaller in the lines containing the suppression constructs than in the control. Ear heights were shorter in the cesA1 and cesA5 containing lines. The average cellulose percentage of total dry matter is normally 46% in control plants. All of the cesA constructs had lines that were below 46% cellulose with cesA1>cesA5>cesA8>cesA4. The lines that exhibited low cellulose percentages were tested by DNA Southern blot analyses to determine which contained a single-copy transgene insertion. All had at least one line that had both low cellulose and a single transgene.

TABLE 9

Summary of CesA Suppression By EL Constructs

| Construct | height (cm) | Ear (cm) | Stalk (mm) | Cellulose <46% | Single transgene |
|---|---|---|---|---|---|
| Control | 171 | 44 | 16 | | |
| CesA1 | 150 | 40 | 14 | 9 | 3 |
| CesA4 | 164 | 46 | 13 | 3 | 2 |
| CesA5 | 148 | 41 | 13 | 7 | 2 |
| CesA8 | 166 | 46 | 15 | 5 | 1 |

These results show that cellulose levels are altered in plants containing cesA gene fragments contained within 1×EL constructs. This is interpreted as meaning that cesA suppression in maize has a detectable phenotype, and that EL-controlled suppression is active in maize. It should be noted that the f3.7 promoter is a weak promoter compared to others used in this application (35S-CaMV, Kti, etc.) and that cesA is a large multigene family. These factors may have an effect on the frequency and/or extent of suppression.

Example 13

Transient Suppression of GFP in Maize Using GUS Complementary Region

All expression cassettes used in this example comprise a maize ubiquitin promoter (nt 1-899), a maize ubiquitin 5' untranslated leader sequence (nt 900-982) and a maize ubiquitin intron 1 (nt 983-1992). In plasmid PHP7921 the coding sequence (nt 2015-2731) is GFP (green fluorescent protein) with codons optimized for expression in maize. In plasmid PHP3953 the coding sequence (nt 2013-3821) is GUS. Both cassettes include the polyadenylation signal sequences from the proteinase inhibitor II gene of *S. tuberosum* (PINII TERM, nt 2737-3047 in PHP7921 and nt 3883-4192 in PHP3953).

Standard recombinant DNA methodologies well known to those skilled in the art were used throughout the construction of the expression cassettes for this work. Orientations of fragment insertions and the final structures of the plasmid constructs were determined using standard agarose gel analysis and/or sequencing of the plasmids.

Plasmid PHP7921 was used to create a complementary region (CR) of a small portion of the GFP coding sequence as follows: plasmid DNA was digested with XhoI and treated with the Klenow fragment of DNA polymerase I to release a 244 bp blunt-ended fragment representing nt 2436-2675 near the 3' end of the GFP coding sequence. This fragment was then inserted back into PHP7921 at the HpaI site (nt 2735) just downstream of the stop codon of GFP. A recombinant plasmid was identified that had the inserted fragment in the reverse orientation relative to the original sequence. This plasmid was designated PHP16391.

Expression cassettes for GUS containing a heterologous GFP-CR were constructed as follows: the entire GFP-CR of PHP16391 was isolated as a BsrGI fragment (nt 2464-2947, 483 bp). This fragment comprises sequences capable of forming a CR with a 214 bp stem and a 55 nt loop. The fragment was rendered blunt-ended as above using Klenow and inserted into the GUS expression cassette of PHP3953 at three different sites. Plasmid PHP16561 has the GFP-CR inserted in the BamHI site (filled in) of PHP3953 (nt 2006), just 5' to the start codon. Plasmid PHP16562 has the GFP-CR inserted in the PacI site (T4 polymerase-treated to render blunt) at nt 3919 of PHP3953 just 3' to the stop codon. Similarly, plasmid PHP16563 has the GFP-CR inserted in the SnaBI site at nt 2398 of PHP3953 within the GUS coding sequence.

High type II callus was maintained by subculturing onto fresh 560P (N6 salts, Erikkson's vitamins, 0,69 g/l proline, 2 mg/l 2,4-D and 3% sucrose) medium every two weeks. Healthy callus was extruded through a 0.77 mm$^2$ nylon mesh, weighed, and resuspended in MS culture medium with 2 mg/l 2,4-D at a density of 3 grams of tissue/40 ml medium. Cells were uniformly suspended by pipetting the solution up-and-down through a large-bore pipette, and 4 ml aliquots (300 mg) were then collected on glass filter papers using a vacuum apparatus. These filters, each containing approximately 300 mg of cells, were then placed on 560P medium and cultured in the dark at 26° C. After 2-4 days the filters were removed from the culture medium and excess liquid was removed using a vacuum apparatus. DNA was then delivered into the cells using a DuPont Biolistics particle gun using a standard Hi-II bombardment transformation protocol (Songstad D. D. et al, In Vitro Cell Dev. Biol. Plant 32:179-183, 1996) modified by using 1 um gold particles. Immediately after bombardment the filters were returned to 560P culture medium and cultured in the dark at 26° C. All DNA's were combined in equal ratios to obtain a final concentration of 1 ug of total DNA/particle preparation (0.33 ug of each DNA combined in each preparative tube was used for 6 shots). The experiment was shot as follows: From each treatment 10 plates were bombarded (5 from each of two DNA preps).

| Treatment | DNA's |
|---|---|
| #1 Control | PHP3953 (GUS) + PHP10256(rLuciferase) + PHP7921 (GFP) |
| #2 GUS w/5'CRC | PHP3953 (GUS) + PHP10256 (rLuciferase) + PHP16561(CR-GUS) |
| #3 GUS w 3' CRC | PHP3953 (GUS) + PHP10256 (rLuciferase) + PHP16562(GUS-CR) |
| #4 GUS w/CRC in cds | PHP3953 (GUS) + PHP10256 (rLuciferase) + PHP16563(GU-CR-S) |

For analysis, the plates within a treatment were grouped into 5 pairs (each pair containing plates shot with different DNA preparations for the same plasmid treatment). Two days after bombardment, all the tissue from the two paired plates was combined and resuspended in 5 ml of culture medium. After mixing with a wide-bore pipette, a 1 ml aliquot was transferred into a 1.5 ml Eppendorf tube. The cells were centrifuged at 1000 RPMs for 2 minutes in a microfuge and the supernatant (culture medium) decanted. To each tube, 150 ul of "Promega Luciferase Passive Lysis Buffer" was added, temperature-equilibrated on ice, and the cells were broken apart using a hand-drill powered Kontes-tube plastic pestil (extraction and subsequent luciferase assays followed Promega's Dual-Luciferase Reporter Assay protocol (Technical Bulletin #TM040). The cell debris was pelleted by centrifugation in the Microfuge at 3000 RPM for 3 minutes and the supernatant was pipetted off. Aliquots of this extract were used for the fluorometric quantitation of both GUS and luciferase (50 and 20 ul, respectively). GUS enzyme activity was determined as a rate measurement between 10 and 40 minutes after adding substrates, and data was expressed as pmol MU/min/ml/extract (slope). Fluorometric GUS assays were performed on a LabSystems FLUOROSKAN Ascent FL according to the protocol of Rao and Flynn (Biotechniques 1990 8:38-40. Fluorometric analysis of luciferase activity collected using an Analytical Luminescence Laboratory Monolight 2010, following the manufacturer's instructions and the Promega protocol. Assessing both markers for each replicate provided an internal control (luciferase) against which relative GUS activity could be rated. Thus, data was plotted as the ratio of GUS/Luciferase units (because the absolute fluorometric units for Renilla luciferase were so high, all the raw values for luciferase activity were divided by 10 before using to normalize GUS activity).

TABLE 10

Complementary Regions of GFP Reduce Target GUS Activity in a 3' (#3) and Internal Orientation (#4)

| Treatment | Pmol. MU/min/ml extract slope/rLuci Ave. | Standard deviation |
|---|---|---|
| #1 | 74.14 | 27.66 |
| #2 | 82.05 | 20.99 |
| #3 | 20.22 | 17.87 |
| #4 | 9.67 | 3.02 |

Repeat Expt

| Treatment | Pmol. MU/min/ml extract slope/rLuci Ave. | Standard deviation |
|---|---|---|
| #1 | 86.93 | 6.94 |
| #2 | 77.3 | 22.62 |
| #3 | 20.03 | 7.32 |
| #4 | 11.2 | 2.32 |

It appears from the results (see Table 10) of these transient expression experiments that the placement of a complementary region 5' to a target does not reduce the expression of the target gene. However, it is believed that under optimized conditions, or in a stable transformation experiment, placement of a complementary region 5' to a target is sufficient to reduce expression of the target.

Example 14

Suppression of Maize PDS by a Modified Soybean Complementary Region

An additional suppression construct was created using a 205 bp HindIII-BstEII fragment from the soybean Kti promoter as the complementary region surrounding a multiple cloning site. Two copies of the Kti fragment were ligated in an inverted repeat arrangement and subsequently modified by PCR to remove inconvenient restriction sites and add cloning sites at both ends and in the region between the two complementary sequences to form the SHH3 cassette (see SEQ ID NO:34). The resulting plasmid (PHP17962) was used as a source of the SHH3 sequence. The Kti sequence is not normally found in the maize genome, therefore no suppression of endogenous maize genes is expected from the SHH3 region alone. However, when a portion of an endogenous target sequence is inserted into the cloning sites between the complementary Kti sequences, the homologous endogenous gene transcript should be affected.

To test the utility of the SHH3 in silencing an endogenous gene, a 1385 bp NheI fragment representing about 80% of the coding sequence of the phytoene desaturase gene (PDS-1) of *Z. mays* (Pioneer EST cnlcz91R, Genbank Accession No. L39266) was treated with Klenow enzyme as previously described to render the ends blunt and then ligated into the EcoRV site of SHH3 to generate PHP17894. The SHH3-PDS fragment was then moved as a 1865 bp HpaI fragment into an intermediate vector construct to place it under the control of the ubiquitin promoter:ubiquitin intron 1 (U.S. Pat. Nos. 5,510,474 and 5,614,399) with polyadenylation signals provided by the pinII terminator (An et al (1989) *Plant Cell* 1: 115-122). The resulting plant transcription unit was moved into a binary vector (PHP15578) containing a CaMV35S-bialaphos selectable marker element to generate PHP17914. This construct was electroporated into competent cells of *Agrobacterium tumefaciens* strain LBA4404 carrying the superbinary plasmid pSB1 ((Ishida et al (1996) *Nature Biotech* 14:745-750). This process generates a cointegrate plasmid comprising the combined sequences of PHP17914 and pSB1. This cointegrate plasmid, designated PHP17939, was used to transform immature embryos of *Z. mays* as follows.

Transformation of Maize Mediated by *Agrobacterium*

Freshly isolated immature embryos of maize, about 10 days after pollination (DAP), were incubated with the *Agrobacterium*. The preferred genotype for transformation is the highly transformable genotype Hi-II (Armstrong (1991) *Maize Gen Coop Newsletter* 65:92-93). An $F_1$ hybrid created by crossing with an Hi-II with an elite inbred may also be used. After *Agrobacterium* treatment of immature embryos, the embryos were cultured on medium containing toxic levels of herbicide. Only those cells which receive the herbicide-resistance gene, and the linked gene(s), grow on selective medium. Transgenic events so selected are propagated and regenerated to whole plants, produce seed, and transmit transgenes to progeny.

Preparation of *Agrobacterium*

The engineered *Agrobacterium tumefaciens* LBA4404 was constructed as per U.S. Pat. No. 5,591,616 to contain the PDS gene suppressed by the complementary region shown in SEQ ID NO:34 and a selectable marker gene. Typically either BAR (D'Halluin et al (1992) *Methods Enzymol.* 216:415-426) or PAT (Wohlleben et al (1988) *Gene* 70:25-37) may be used as a selectable marker.

To use the engineered construct in plant transformation, a master plate of single bacterial colonies was first prepared by inoculating the bacteria on minimal AB medium [minimal AB medium contains the following ingredients: 850.000 ml of deionized water; 50.000 ml of stock solution 800A; 9 g of Phytagar which is added after Q.S. to volume; 50.000 ml of stock solution 800B #; 5.000 g of glucose #; and 2.000 ml of spectinomycin 50/mg/ml stock #. Directions are: dissolve ingredients in polished deionized water in sequence; Q.S. to volume with polished deionized water less 100 ml per liter; sterilize and cool to 60° C. Ingredients designated with a # are added after sterilizing and cooling to temperature. Stock solution 800A contains the following ingredients: 950.000 ml of deionized water; 60.000 g of potassium phosphate dibasic K2HPO4; and 20.000 g of sodium phos. monobasic, hydrous. Directions are: dissolve ingredients in polished deionized water in sequence; adjust pH to 7.0 with potassium hydroxide; Q.S. to volume with polished deionized water after adjusting pH; and sterilize and cool to 60° C. Stock solution 800B contains the following ingredients: 950.000 ml of deionized water; 20.000 g of ammonium chloride; 6.000 g of magnesium sulfate 7-H2O, MgSO4, 7H2O; 3.000 g of potassium chloride; 0.200 g of calcium chloride (anhydrate); and 0.050 g of ferrous sulfate 7-hydrate. Directions are: dissolve ingredients in polished deionized water in sequence; Q.S. to volume with polished deionized water; and sterilize and cool to 60° C.] and then incubating the bacteria plate inverted at 28° C. in darkness for about 3 days. A working plate was then prepared by selecting a single colony from the plate of minimal A medium [minimal A medium contains the following ingredients: 950.000 ml of deionized water; 10.500 g of potassium phosphate dibasic K2HPO4; 4.500 g of potassium phosphate monobasic KH2PO4; 1.000 g of ammonium sulfate; 0.500 g of sodium citrate dihydrate; 10.000 ml of sucrose 20% solution #; and 1.000 ml of 1M magnesium sulfate #. Directions are: dissolve ingredients in polished deionized water in sequence; Q.S. to volume with deionized water; sterilize and cool to 60° C. Ingredients designated with a # are added after sterilizing and cooling to temperature] and streaking it across a plate of YP medium [minimal YP medium contains the following ingredients: 950.000 ml of deionized water; 5.000 g of yeast extract (Difco); 10.000 g of peptone (Difco); 5.000 g of sodium chloride; 15.000 g of bacto-agar, which is added after Q.S. to volume; and 1.000 ml of spectinomycin 50 mg/ml stock #. Directions are: dissolve ingredients in polished deionized water in sequence; adjust pH to 6.8 with potassium hydroxide; Q.S. to volume with polished deionized water after adjusting pH; sterilize and cool to 60° C. Ingredients designated with a # are added after sterilizing and cooling to temperature]. The YP-medium bacterial plate was then incubated inverted at 28° C. in darkness for 1-2 days.

*Agrobacterium* for plant transfection and co-cultivation was prepared 1 day prior to transformation. Into 30 ml of minimal A medium in a flask was placed 50 μg/ml spectinomycin, 100 μM acetosyringone, and about a ⅛ loopful of *Agrobacterium* from a 1 to 2-day-old working plate. The *Agrobacterium* was then grown at 28° C. at 200 rpm in darkness overnight (about 14 hours). In mid-log phase, the *Agrobacterium* was harvested and resuspended at 3 to $5\times10^8$ CFU/ml in 561Q medium+100 μM acetosyringone using standard microbial techniques and standard curves.

Immature Embryo Preparation

Nine to ten days after controlled pollination of a corn plant, developing immature embryos are opaque and 1-1.5 mm long and are the appropriate size for Agro-infection. The husked ears were sterilized in 50% commercial bleach and 1 drop Tween for 30 minutes, and then rinsed twice with sterile water. The immature embryos were aseptically removed from the caryopsis and placed into 2 ml of sterile holding solution comprising of medium 561Q+100 μM acetosyringone [medium 561 Q contains the following ingredients: 950.000 ml of D-I Water, Filtered; 4.000 g of Chu (N6) Basal Salts (Sigma C-1416); 1.000 ml of Eriksson's Vitamin Mix (1000× Sigma-1511); 1.250 ml of Thiamine.HCL.4 mg/ml; 3.000 ml of 2,4-D 0.5 mg/ml (No. 2A); 0.690 g of L-proline; 68.500 g of Sucrose; and 36.000 g of Glucose. Directions are: dissolve ingredients in polished deionized water in sequence; adjust pH to 5.2 w/KOH; Q.S. to volume with polished deionized water after adjusting pH; and filter sterilize (do not autoclave)].

*Agrobacterium* Infection and Co-Cultivation of Embryos

Holding solution was decanted from excised immature embryos and replaced with prepared *Agrobacterium*. Following gentle mixing and incubation for about 5 minutes, the *Agrobacterium* was decanted from the immature embryos. Immature embryos were then moved to a plate of 562P medium [medium 562 P contains the following ingredients: 950.000 ml of D-I Water, Filtered; 4.000 g of Chu (N6) Basal Salts (Sigma C-1416); 1.000 ml of Eriksson's Vitamin Mix (1000× Sigma-1511); 1.250 ml of Thiamine.HCL.4 mg/ml; 4.000 ml of 2,4-D 0.5 mg/ml; 0.690 g of L-proline; 30.000 g of Sucrose; 3.000 g of Gelrite, which is added after Q.S. to volume; 0.425 ml of Silver Nitrate 2 mg/ml #; and 1.000 ml of Aceto Syringone 100 mM #. Directions are: dissolve ingredients in polished deionized water in sequence; adjust pH to 5.8 w/KOH; Q.S. to volume with polished deionized water after adjusting pH; and sterilize and cool to 60° C. Ingredients designated with a # are added after sterilizing and cooling to temperature], scutellum surface upwards, and incubated at 20° C. for 3 days in darkness followed by incubation at 28° C. for 3 days in darkness on medium 562P+100 mg/ml carbenecillin (see U.S. Pat. No. 5,981,840).

Selection of Transgenic Events

Following incubation, the immature embryos were transferred to 563O medium [medium 563 O contains the following ingredients: 950.000 ml of D-I Water, Filtered; 4.000 g of Chu (N6) Basal Salts (Sigma C-1416); 1.000 ml of Eriksson's Vitamin Mix (1000× Sigma-1511); 1.250 ml of Thiamine-.HCL.4 mg/ml; 30.000 g of Sucrose; 3.000 ml of 2,4-D 0.5 mg/ml (No. 2A); 0.690 g of L-proline; 0.500 g of Mes Buffer; 8.000 g of Agar (Sigma Δ-7049, Purified), which is added after Q.S. to volume; 0.425 ml of Silver Nitrate 2 mg/ml #; 3.000 ml of Bialaphos 1 mg/ml #; and 2.000 ml of Agribio Carbenicillin 50 mg/ml #. Directions are: dissolve ingredients in polished deionized water in sequence; adjust to pH 5.8 w/koh; Q.S. to volume with polished deionized water after adjusting pH; sterilize and cool to 60° C. Ingredients designated with a # are added after sterilizing and cooling to temperature] for selection of events. The transforming DNA possesses a herbicide-resistance gene, in this example the BAR gene, which confers resistance to bialaphos. At 10- to 14-day intervals, embryos were transferred to 563O medium. Actively growing putative transgenic embryogenic tissue were visible in 6-8 weeks.

Example 15

Suppression of Maize PDS by a Modified Soybean Complementary Region Regeneration of $T_0$ Plants Transgenic embryogenic tissue is transferred to 288W medium [medium 288 W contains the following ingredients: 950.000 ml of D-I $H_2O$; 4.300 g of MS Salts; 0.100 g of Myo-Inositol; 5.000 ml of MS Vitamins Stock Solution (No. 36J); 1.000 ml of Zeatin.5 mg/ml; 60.000 g of Sucrose; 8.000 g of Agar (Sigma A-7049, Purified), which is added after Q.S. to volume; 2.000 ml of IAA 0.5 mg/ml #; 1.000 ml of 0.1 Mm ABA #; 3.000 ml of Bialaphos 1 mg/ml #; and 2.000 ml of Agribio Carbenicillin 50 mg/ml #. Directions are: dissolve ingredients in polished deionized water in sequence; adjust to pH 5.6; Q.S. to volume with polished deionized water after adjusting pH; sterilize and cool to 60° C. Add 3.5 g/L of Gelrite for cell biology. Ingredients designated with a # are added after sterilizing and cooling to temperature] and incubated at 28° C. in darkness until somatic embryos matured, or about 10 to 18 days. Individual matured somatic embryos with well-defined scutellum and coleoptile are transferred to 272 embryo germination medium [medium 272 contains the following ingredients: 950.000 ml of deionized water; 4.300 g of MS Salts; 0.100 g of Myo-Inositol; 5.000 of MS Vitamins Stock Solution; 40.000 g of Sucrose; and 1.500 g of Gelrite, which is added after Q.S. to volume. Directions are: dissolve ingredients in polished deionized water in sequence; adjust to pH 5.6; Q.S. to volume with polished deionized water after adjusting pH; and sterilize and cool to 60° C.] and incubated at 28° C. in the light. After shoots and roots emerge, individual plants are potted in soil and hardened-off using typical horticultural methods. Plants are then evaluated for the PDS-silenced phenotype.

Phytoene desaturase catalyzes a rate-limiting step in the biosynthesis of carotenoids in plants (Misawa, et al *The Plant Journal* (1993) 4(5):833-840). It is a known target of bleaching herbicides such as norflurazon. Cosuppression of the endogenous phytoene desaturase by the introduced SHH3-flanked PDS 1 gives a similar bleached phenotype when young plants are incubated in the light (Thomas, et al (2001) *The Plant Journal* 25(4):417-425; Kumagi et al (1995) *PNAS USA* 92:1679-1683; Ruiz et al (1998) *Plant Cell* 10:937-946).

What is claimed is:
1. A recombinant construct comprising SEQ ID NO:13.
2. A vector comprising the recombinant construct of claim 1.

* * * * *